(12) United States Patent
Wang et al.

(10) Patent No.: US 6,667,336 B2
(45) Date of Patent: Dec. 23, 2003

(54) GLYT-1 INHIBITORS

(75) Inventors: Zhaoqing Wang, Greenwood, IN (US); William Delaney, Bear, DE (US); Ashok Tehim, Ridgewood, NJ (US); Shawn Maddaford, Mississauga (CA); Ian Egle, Mississauga (CA); Richard Schumacher, Monroe, NY (US); Allen T. Hopper, Glen Rock, NJ (US)

(73) Assignees: NPS Allelix Corp., Mississauga; Allelix Neuroscience, Inc., Salt Lake City, UT (US)

( * ) Notice: Subject to any disclaimer, the term of this patent is extended or adjusted under 35 U.S.C. 154(b) by 0 days.

(21) Appl. No.: 10/077,579

(22) Filed: Feb. 15, 2002

(65) Prior Publication Data

US 2003/0176489 A1 Sep. 18, 2003

(51) Int. Cl.$^7$ ............... A61K 31/38; C07D 333/22; C07D 409/00
(52) U.S. Cl. ............... 514/444; 514/438; 549/77; 549/59
(58) Field of Search ............... 514/444, 438; 549/59, 77

(56) References Cited

U.S. PATENT DOCUMENTS

| | | |
|---|---|---|
| 4,383,999 A | 5/1983 | Bondinell et al. |
| 4,514,414 A | 4/1985 | Bondinell et al. |
| 4,639,468 A | 1/1987 | Roncucci et al. |
| 4,772,615 A | 9/1988 | Pavia |
| 4,931,450 A | 6/1990 | Sonnewald |
| 5,010,090 A | 4/1991 | Gronvald et al. |
| 5,837,730 A | 11/1998 | Javitt |
| 6,103,743 A * | 8/2000 | Bell et al. .................. 514/357 |
| 6,191,165 B1 | 2/2001 | Ognyanov et al. |
| 6,274,584 B1 * | 8/2001 | Peschke et al. ........ 514/255.01 |
| 6,350,907 B1 * | 2/2002 | Fray et al. ................ 562/623 |

FOREIGN PATENT DOCUMENTS

| | | |
|---|---|---|
| BE | 885 303 | 3/1981 |
| DE | 30 10 599 | 10/1980 |
| EP | 0 066 456 | 12/1982 |
| EP | 0 221 572 | 5/1987 |
| EP | 0 528 172 | 2/1993 |
| EP | 0 231 996 | 8/1998 |
| JP | 02-129158 | 5/1990 |

OTHER PUBLICATIONS

Fadia E. Ali et al., J. Med. Chem., 28, 653–660 (1985).
P. O. Edlund, Journal of Mass Spectrometry, 30:1380–1392 (1995).
Michael R. Pavia et al., J. Med. Chem., 35:4238–4248 (1992).
Inayama, et al., Chem. Pharm. Bull. 28 (9) 2779–2782 (1980).
Elena Carceller, et. al., J. Med. Chem., 36, 4238–4248 (1992).
Michel Vaultier, et. al., Tetrahedron, 35, 1357–1364 (1979).
Chemical Abstracts, citation 5199 g, vol. 64, Cyclization at carbon–carbon double bond. II. Synthesis of 4 substituted prlines by Pictet–Spengler reaction. p. 5199 (1966).

* cited by examiner

Primary Examiner—Deborah C. Lambkin
(74) Attorney, Agent, or Firm—Dechert LLP

(57) ABSTRACT

The invention provides a pharmaceutical for treatment of neurological and neuropsychiatric disorders comprising a compound of the formula:

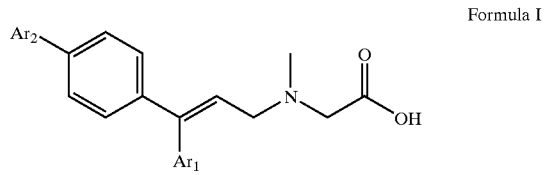

Formula I or a pharmaceutically acceptable salt thereof.

66 Claims, No Drawings

GLYT-1 INHIBITORS

The present invention relates to a class of substituted amines, to pharmaceutical compositions containing them and to methods of treating neurological and neuropsychiatric disorders using such compounds.

Synaptic transmission is a complex form of intercellular communication that involves a considerable array of specialized structures in both the pre- and post-synaptic terminal and surrounding glial cells (Kanner and Schuldiner, *CRC Critical Reviews in Biochemistry*, 22, 1987:1032). Transporters sequester neurotransmitters from the synapse, thereby regulating the concentration of neurotransmitters in the synapse, as well as their duration therein, which together influence the magnitude of synaptic transmission. Further, by preventing the spread of neurotransmitter to neighbouring synapses, transporters maintain the fidelity of synaptic transmission. Lastly, by sequestering released neurotransmitter into the presynaptic terminal, transporters allow for neurotransmitter reutilization.

Neurotransmitter transport is dependent upon extracellular sodium and the voltage difference across the membrane. Under conditions of intense neuronal firing, for example, during a seizure, transporters can function in reverse, releasing neurotransmitter in a calcium-independent non-exocytotic manner (Attwell et al., *Neuron*, 11, 1993:401–407). Pharmacologic modulation of neurotransmitter transporters thus provides a means for modifying synaptic activity, which provides useful therapy for the treatment of neurological and psychiatric disturbances.

The amino acid glycine is a major neurotransmitter in the mammalian nervous system, functioning at both inhibitory and excitatory synapses. By nervous system, both the central and peripheral portions of the nervous system are intended. These distinct functions of glycine are mediated by two different types of receptor, each of which is associated with a different class of glycine transporter. The inhibitory actions of glycine are mediated by glycine receptors that are sensitive to the convulsant alkaloid strychnine, and are thus referred to as "strychnine-sensitive". Such receptors contain an intrinsic chloride channel that is opened upon binding of glycine to the receptor; by increasing chloride conductance, the threshold for firing of an action potential is increased. Strychnine-sensitive glycine receptors are found predominantly in the spinal cord and brainstem, and pharmacological agents that enhance the activation of such receptors will thus increase inhibitory neurotransmission in these regions.

Glycine also functions in excitatory transmission by modulating the actions of glutamate, the major excitatory neurotransmitter in the central nervous system (Johnson and Ascher, *Nature*, 325, 1987:529–531; Fletcher et al., *Glycine Transmission*, Otterson and Storm-Mathisen, eds., 1990:193–219). Specifically, glycine is thought to be an obligatory co-agonist at the class of glutamate receptor termed N-methyl-D-aspartate (NMDA) receptor. Activation of NMDA receptors increases sodium and calcium conductance, which depolarizes the neuron, thereby increasing the likelihood that it will fire an action potential.

NMDA receptors in the hippocampal region of the brain play an important role in a model of synaptic plasticity known as long-term potentiation (LTP), which is integral in certain types of learning and memory (Hebb, D. O (1949) *The Organization of Behavior*, Wiley, N Y; Bliss and Collingridge (1993) *Nature* 361: 31–39; Morris et al. (1986) *Nature* 319: 774–776). Enhanced expression of selected NMDA receptor sub-units in transgenic mice results in increased NMDA-receptor-mediated currents, enhanced LTP, and better performance in some tests of learning and memory (Tang et al. (1999) *Nature* 401: 63).

Conversely, decreased expression of selected NMDA receptor sub-units in transgenic mice produces behaviors similar to pharmacologically-induced animal models of schizophrenia, including increased locomotion, increased stereotypy, and deficits in social/sexual interactions (Mohn et al. (1999) *Cell* 98:427–436). These aberrant behaviors can be ameliorated using the antipsychotics haloperidol and clozapine.

NMDA receptors are widely distributed throughout the brain, with a particularly high density in the cerebral cortex and hippocampal formation.

Molecular cloning has revealed the existence of two classes of glycine transporters in mammalian brains, termed GlyT-1 and GlyT-2. GlyT-1 is found throughout the brain and spinal cord, and it has been suggested that its distribution corresponds to that of glutamatergic pathways and NMDA receptors (Smith, et al., *Neuron*, 8, 1992:927–935). Molecular cloning has further revealed the existence of four variants of GlyT-1, termed GlyT-1a, GlyT-1b, GlyT-1c and GlyT-1d. Two of these variants (1a and 1b) are found in rodents, each of which displays a unique distribution in the brain and peripheral tissues (Borowsky et al., *Neuron*, 10, 1993:851–863; Adams et al., i J. Neuroscience, 15, 1995:2524–2532). The third variant, 1c, has only been detected in human tissues (Kim, et al., *Molecular Pharmacology*, 45, 1994:608–617). The fourth variant has been detected in human tissues (see U.S. Pat. No. 6,008, 015). These variants arise by differential splicing and exon usage, and differ in their N-terminal regions. GlyT-2, is found predominantly in the brain stem and spinal cord, and its distribution corresponds closely to that of strychnine-sensitive glycine receptors (Liu et al., *J. Biological Chemistry*, 268, 1993:22802–22808; Jursky and Nelson, *J. Neurochemistry*, 64, 1995:1026–1033). Another distinguishing feature of glycine transport mediated by GlyT-2 is that it is not inhibited by sarcosine as is the case for glycine transport mediated by GlyT-1. These data are consistent with the view that, by regulating the synaptic levels of glycine, GlyT-1 and GlyT-2 selectively influence the activity of NMDA receptors and strychnine-sensitive glycine receptors, respectively.

Compounds which inhibit or activate glycine transporters would thus be expected to alter receptor function by modifying glycine concentrations in the synapse and, thus, provide therapeutic benefits in a variety of disease states.

For example, compounds which inhibit GlyT-1 mediated glycine transport may increase glycine concentrations at NMDA receptors, which receptors are located in the forebrain, among other locations. This concentration increase could perhaps elevate the activity of NMDA receptors, thereby possibly alleviating symptoms of schizophrenia and enhancing cognitive function. Alternatively, compounds that interact directly with the glycine receptor component of the NMDA receptor can have the same or similar effects as increasing or decreasing the availability of extracellular glycine caused by inhibiting or enhancing GlyT-1 activity, respectively. See, for example, Pitkänen et al., *Eur. J. Pharmacol.*, 253,125–129 (1994); Thiels et al., *Neuroscience*, 46, 501–509 (1992); and Kretschmer and Schmidt, *J. Neurosci.*, 16, 1561–1569 (1996).

It has been found that many compounds which are effective in binding to and inhibiting the GlyT-1 transporter, also display toxic effects when administered in vivo. While such compounds are useful pharmaceutical tools for studying the function of the transporters, toxicity would limit the usefulness of such compounds as pharmaceuticals.

Hence it is desirable to provide compounds that affect glycine transport. Also, it is desirable to provide compounds which affect glycine transport but which are sufficiently non-toxic so as to be useful in pharmaceutical compositions.

SUMMARY OF THE INVENTION

The present invention is directed to compounds which have been found to be effective in inhibiting GlyT-1 transport and are sufficiently non-toxic as to be medically useful. More particularly, the compounds of the invention show an unexpected improved toxicity profile over other known GlyT-1 inhibitors. According to one aspect of the invention, there are provided compounds of Formula I:

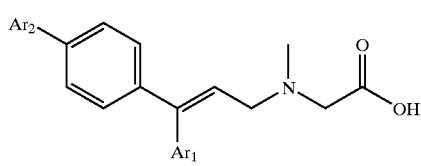

Formula I wherein:
  $Ar^1$ is a thiophene group which may be 2 or 3 thiophene and is optionally substituted with up to one substituent selected from methyl or ethyl; and
  $Ar_2$ is selected from thiophene, furan and substituted phenyl, wherein the substituted on the phenyl group is selected from $C_{1-6}$ alkyl, halo, $C_{1-6}$ haloalkyl, $C_{1-6}$ alkoxy, $C^{1-6}$ haloalkoxy, cyano,
and a salt, solvate and hydrate thereof.

In Accordance with a further aspect of the invention there is provided the compound: (Z)-N-(1-(4-(3-Thienyl)phenyl)-1-(2-methylphenyl)prop-1-en-3-yl)sarcosine.

It has been found that compounds of Formula I and the compound (Z)-N-(1-(4-(3-Thienyl)phenyl)-1-(2-methylphenyl)prop-1-en-3-yl)sarcosine, inhibit glycine transport via GlyT-1, or are precursors (for example, prodrugs) of such compounds. GlyT-1 transport inhibitors are useful in the treatment of schizophrenia, as well as other CNS-related disorders such as cognitive dysfunction, dementia (including that related to Alzheimer's disease), attention deficit disorder, depression, and pervasive developmental disorders such as autistic disorder, Rett's disorder, childhood disintegrative disorder, Asperger's disorder and pervasive developmental disorders not otherwise specified (for example atypical autism).

According to another aspect of the invention there is provided a composition comprising a compound of formula 1 or the compound (z)-N-(1-(4-(3-Thienyl)phenyl)-1-(2-methylphenyl)prop-1-en-3-yl)sarcosine, and a carrier.

According to another aspect of the invention, there is provided a pharmaceutical composition comprising a compound of Formula I and a pharmaceutically acceptable carrier. In a further aspect of the invention there is provided a pharmaceutical composition comprising a compound of formula 1 in an amount effective to inhibit glycine transport, and a pharmaceutically acceptable carrier.

In a further aspect of the invention there is provided a pharmaceutical composition comprising the compound (Z)-N-(1-(4-(3-Thienyl)phenyl)-1-(2-methylphenyl)prop-1-en-3-yl)sarcosine and a pharmaceutically aceptable carrier. In still a further aspect of the invention there is provided a pharmaceutical composition comprising the compound (Z)-N-(1-(4-(3-Thienyl)phenyl)-1-(2-methylphenyl)prop-1-en-3-yl)sarcosine in a amount effective to inhibit glycine transport and a pharmaceutically acceptable carrier.

In another aspect of the invention, there are provided compositions containing compounds of Formula 1 or the compound (Z)-N-(1-(4-(3-Thienyl)phenyl)-1-(2-methylphenyl)prop-1-en-3-yl)sarcosine in amounts suitable for pharmaceutical use to treat medical conditions for which a glycine transport inhibitor is indicated. Preferred are those compositions containing compounds useful in the treatment of medical conditions for which GlyT-1-mediated inhibition of glycine transport is needed, such as the treatment of schizophrenia or cognitive dysfunction.

The compounds of the Formula 1 or the compound (Z)-N-(1-(4-(3-Thienyl)phenyl)-1-(2-methylphenyl)prop-1-en-3-yl)sarcosine can be used for treating a patient having a medical condition for which a glycine transport inhibitor is indicated, which indications are as recited above. A preferred indication is schizophrenia. The compounds can also be used for manufacturing a medicament for treating a patient having a medical condition for which a glycine transport inhibitor is indicated.

DEFINITIONS

The term "alkyl" as used herein means straight- and branched-chain carbon and hydrogen containing radicals with 1, 2, 3, 4, 5 or 6 carbon atoms and includes methyl, ethyl and the like.

The term $C_{1-6}$ as used herein means an alkyl radical of 1, 2, 3, 4, 5, or 6 carbon atoms.

The term "alkoxy" as used herein means straight- and branched-chain alkyl groups terminating in an oxy radicals containing 1, 2, 3, 4, 5, or 6 carbon atoms and includes methoxy, ethoxy, t-butoxy and the like.

The term "halo" as used herein means halogen and includes fluoro, chloro, bromo and the like.

The term "haloalkyl" refers to an alkyl group substituted by one or more independently selected halo atoms, such as —$CF_3$.

Similarly, the term "haloalkoxy" refers to an alkoxy group substituted by one or more independently selected halo atoms, such as —$OCF_3$.

PREFERRED EMBODIMENTS

Suitable embodiments of the invention include compounds of formula 1 wherein $Ar_1$ is selected from optionally substituted 2-thiophene or 3-thiophene. In a suitable embodiment of the invention $Ar_1$ is 2-thiophene. In a preferred embodiment of the invention $Ar_1$, is 2-(3-alkylthiophene) preferably 2-(3-methylthiophene). In another preferred embodiment of the invention Ar1 is 3-thiophene. In a further preferred embodiment $Ar_1$ is 3-(4-alkylthiophene), preferably 3-(4-methylthiophene).

In suitable embodiments of the invention $Ar_2$ is selected from substituted phenyl, thiophene and furan. In a more preferred embodiment of the invention $Ar_2$ is substituted phenyl wherein such substituents are at the 3, or 4 position, and wherein the substituents are selected from: $C_{1-6}$ alkyl; halo; $C_{1-6}$ haloalkyl; $C_{1-6}$ alkoxy; $C_{1-6}$ haloalkoxy; and cyano. In other preferred embodiments, the phenyl substituent at the 3 or 4 position is selected from $CF_3$, Me, iPr, MeO, CN and $CF_3O$. In a preferred embodiment, $Ar_2$ is 3-methoxyphenyl. In another preferred embodiment, $Ar_2$ is 3-methyl phenyl. In yet another preferred embodiment, $Ar_2$ is 3-trifluoromethoxyphenyl. In still another embodiment, $Ar_2$ is 3-triflouromethyl phenyl. In a further preferred embodiment, $Ar_2$ is 4-isopropyl phenyl, and in still another preferred embodiment $Ar_2$ is 3-cyanophenyl.

In suitable embodiments Ar$_2$ is thiophene. In a preferred embodiment of the invention Ar$_2$ is 2-thiophene.

In still another preferred embodiment Ar$_2$ is 2-furan.

More preferred embodiments of the invention include:
(Z)-N-(1-(4-(4-Isopropylphenyl)phenyl)-1-(3-thienyl)prop-1-en-3-yl)sarcosine, (compound G(i));
(Z)-N-(1-(4-(3-Thienyl)phenyl)-1-(3-thienyl)prop-1-en-3-yl)sarcosine, (compound G(ii));
(Z)-N-(1-(4-(2-Thienyl)phenyl)-1-(3-thienyl)prop-1-en-3-yl)sarcosine, (compound G(iii));
(Z)-N-(1-(4-(2-Furyl)phenyl)-1-(3-thienyl)prop-1-en-3-yl)sarcosine, (compound G(iv));
(Z)-N-(1-(4-(3-Methoxyphenyl)phenyl)-1-(3-thienyl)prop-1-en-3-yl)sarcosine, (compound G(v));
(Z)-N-(1-(4-(3-Methylphenyl)phenyl)-1-(3-thienyl)prop-1-en-3-yl)sarcosine, (compound G(vi));
(Z)-N-(1-(4-(3-(Trifluoromethoxy)phenyl)phenyl)-1-(3-thienyl)prop-1-en-3-yl)sarcosine, (compound G(vii));
(Z)-N-(1-(4-(3-Cyanophenyl)phenyl)-1-(3-thienyl)prop-1-en-3-yl)sarcosine, (compound G(viii));
(Z)-N-(1-(4-(3-Thienyl)phenyl)-1-(2-thienyl)prop-1-en-3-yl)sarcosine, (compound G(ix));
(Z)-N-(1-(4-(3-Thienyl)phenyl)-1-(3-(4-methylthienyl))prop-1-en-3-yl)sarcosine, (compound G(x));
(Z)-N-(1-(4-(3-(Trifluoromethyl)phenyl)phenyl)-1-(3-(4-methylthienyl))prop-1-en-3-yl)sarcosine, (compound G(xi));
(Z)-N-(1-(4-(3-Methoxyphenyl)phenyl)-1-(3-(4-methylthienyl))prop-1-en-3-yl)sarcosine, (compound G(xii));
(Z)-N-(1-(4-(3-Methylphenyl)phenyl)-1-(2-(3-methylthienyl))prop-1-en-3-yl)sarcosine, (compound G(xiii));

A most preferred embodiment of the invention is
(Z)-N-(1-(4-(2-Furyl)phenyl)-1-(3-thienyl)prop-1-en-3-yl)sarcosine, (compound G(iv)).

Another suitable embodiment of the invention is the compound
(Z)-N-(1-(4-(3-Thienyl)phenyl)-1-(2-methylphenyl)prop-1-en-3-yl)sarcosine, (compound G(xiv)).

In another embodiment of the invention, the compound of Formula I is provided in labeled form, such as radiolabeled form (e.g. labeled by incorporation within its structure $^3$H or $^{14}$C or by conjugation to $^{125}$I). In a preferred aspect of the invention, such compounds, which bind preferentially to GlyT-1, can be used to identify GlyT-1 receptor ligands by techniques common in the art. This can be achieved by incubating the receptor or tissue in the presence of a ligand candidate and then incubating the resulting preparation with an equimolar amount of radiolabeled compound of the invention. GlyT-1 receptor ligands are thus revealed as those that significantly occupy the GlyT-1 site and prevent binding of the radiolabeled compound of the present invention. Alternatively, GlyT-1 receptor ligand candidates may be identified by first incubating a radiolabeled form of a compound of the invention then incubating the resulting preparation in the presence of the candidate ligand. A more potent GlyT-1 receptor ligand will, at equimolar concentration, displace the radiolabeled compound of the invention.

Base addition salts of the compounds of Formula I are most suitably formed from pharmaceutically acceptable acids. Also included within the scope of the invention are acid addition salts, solvates, and hydrates of compounds of the invention.

The conversion of a given compound salt to a desired compound salt is achieved by applying standard techniques, well known to one skilled in the art.

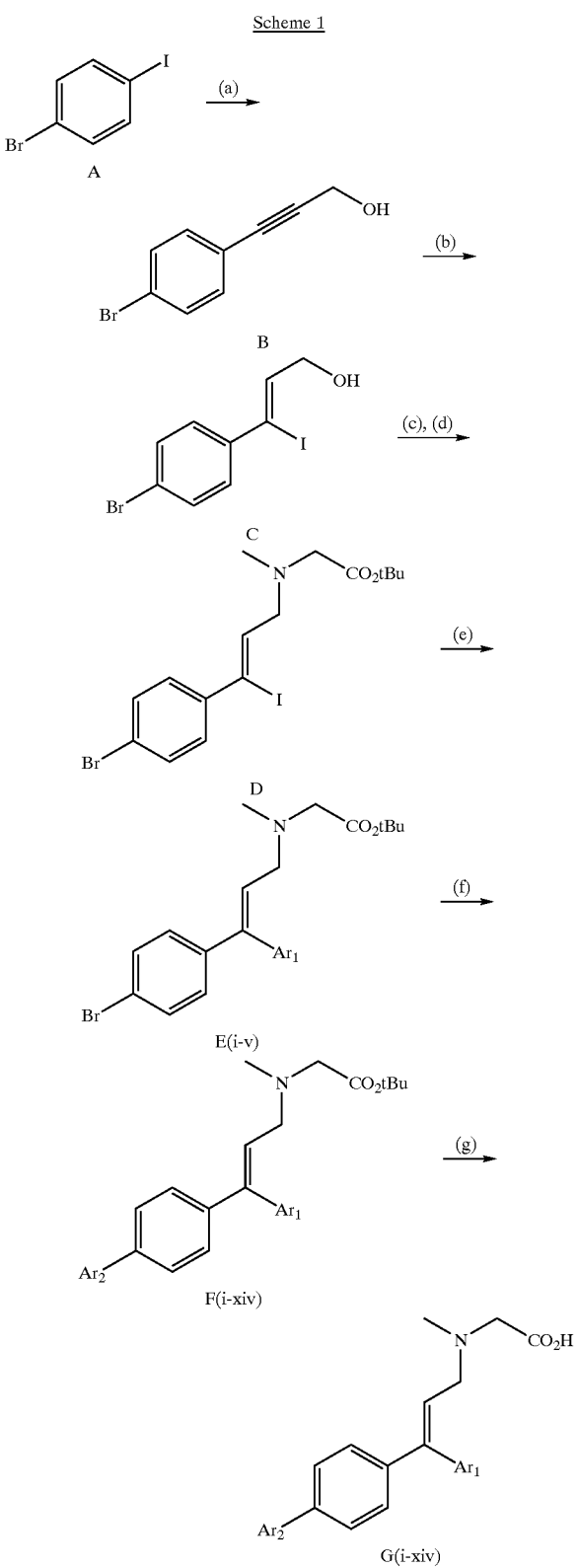

Compounds of Formula 1 are readily prepared by the method shown in Scheme 1 above. Intermediate B was prepared by the palladium catalysed reaction of 4-bromoiodobenzene with propargyl alcohol. Compound B was converted to iodide C by treatment with sodium bis(2- methoxyethoxy)aluminum hydride(Red-Al) followed by iodine. A two step process consisting of conversion of alcohol to bromide followed by displacement with sarcosine led to the intermediate D. Intermediate D is a particularly useful intermediate as it allows the preparation of a number of derivatives where the aryl group can be oriented with complete stereochemical control. For example, common intermediate D was reacted with various boronic acids to yield products of the formula E.

The products of the formula E are also useful chemical intermediates. These products allow the preparation of numerous compounds with 4'-aryl groups (Ar2 groups). The products E are reacted with various boronic acids to yield a variety of products of the formula F which can be deprotected in the last step with formic acid to give the final compounds of type G.

Using the reactions described herein the following compounds of the invention have been made:

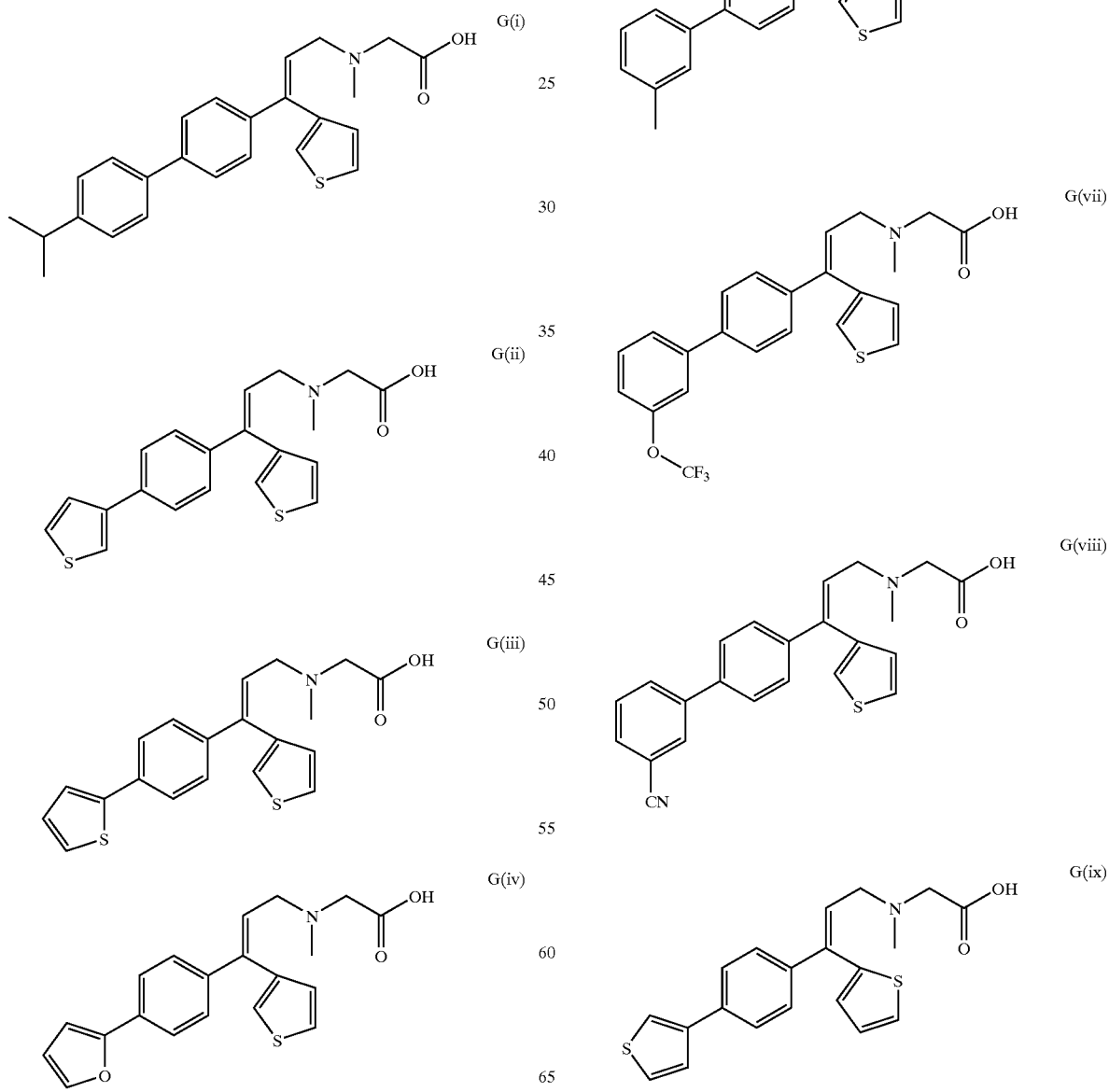

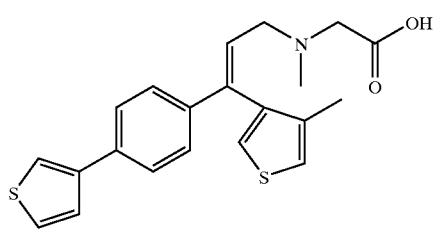

G(x)

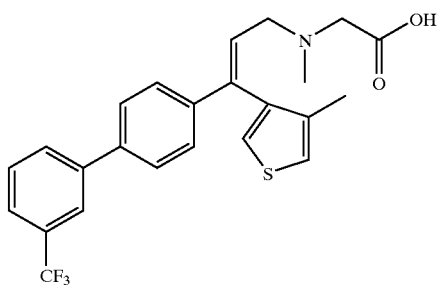

G(xi)

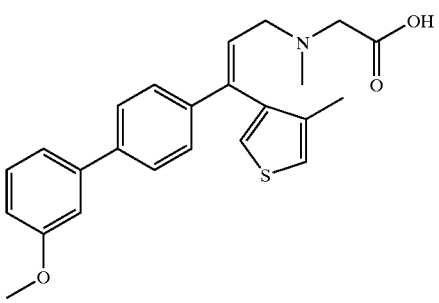

G(xii)

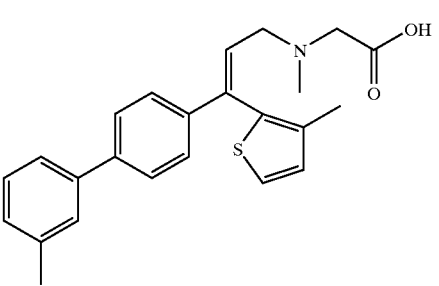

G(xiii)

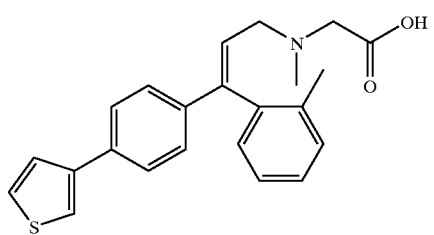

G(xiv)

The compounds of the invention may be administered orally, sublingually, rectally, nasally, vaginally, topically (including the use of a patch or other transdermal delivery device), by pulmonary route by use of an aerosol, or parenterally, including, for example, intramuscularly, subcutaneously, intraperitoneally, intraarterially, intravenously or intrathecally. Administration can be by means of a pump for periodic or continuous delivery. The compounds of the invention may be administered alone, or are combined with a pharmaceutically-acceptable carrier or excipient according to standard pharmaceutical practice. For the oral mode of administration, the compounds of the invention may be used in the form of tablets, capsules, lozenges, chewing gum, troches, powders, syrups, elixirs, aqueous solutions and suspensions, and the like. In the case of tablets, carriers that are used include lactose, sodium citrate and salts of phosphoric acid. Various disintegrants such as starch, and lubricating agents such as magnesium stearate and talc, are commonly used in tablets. For oral administration in capsule form, useful diluents are lactose and high molecular weight polyethylene glycols. If desired, certain sweetening and/or flavoring agents are added. For parenteral administration, sterile solutions of the compounds of the invention are usually prepared, and the pHs of the solutions are suitably adjusted and buffered. For intravenous use, the total concentration of solutes should be controlled to render the preparation isotonic. For ocular administration, ointments or droppable liquids may be delivered by ocular delivery systems known to the art such as applicators or eye droppers. Such compositions can include mucomimetics such as hyaluronic acid, chondroitin sulfate, hydroxypropyl methylcellulose or polyvinyl alcohol, preservatives such as sorbic acid, EDTA or benzylchromium chloride, and the usual quantities of diluents and/or carriers. For pulmonary administration, diluents and/or carriers will be selected to be appropriate to allow the formation of an aerosol.

Suppository forms of the compounds of the invention are useful for vaginal, urethral and rectal administrations. Such suppositories will generally be constructed of a mixture of substances that is solid at room temperature but melts at body temperature. The substances commonly used to create such vehicles include theobroma oil, glycerinated gelatin, hydrogenated vegetable oils, mixtures of polyethylene glycols of various molecular weight and fatty acid esters of polyethylene glycol. See, Remington's Pharmaceutical Sciences, 16th Ed., Mack Publishing, Easton, Pa., 1980, pp. 1530–1533 for further discussion of suppository dosage forms. Analogous gels or creams can be used for vaginal, urethral and rectal administrations.

Numerous administration vehicles will be apparent to those of ordinary skill in the art, including without limitation slow release formulations, liposomal formulations and polymeric matrices.

Examples of pharmaceutically acceptable acid addition salts for use in the present invention include those derived from mineral acids, such as hydrochloric, hydrobromic, phosphoric, metaphosphoric, nitric and sulfuric acids, and organic acids, such as tartaric, acetic, citric, malic, lactic, fumaric, benzoic, glycolic, gluconic, succinic, p-toluenesulphonic and arylsulphonic acids, for example. Examples of pharmaceutically acceptable base addition salts for use in the present invention include those derived from non-toxic metals such as sodium or potassium, ammonium salts and organoamino salts such as triethylamine salts. Numerous appropriate such salts will be known to those of ordinary skill.

The physician or other health care professional can select the appropriate dose and treatment regimen based on the subject's weight, age, and physical condition. Dosages will generally be selected to maintain a serum level of compounds of the invention between about 0.01 µg/cc and about 1000 µg/cc, preferably between about 0.1 µg/cc and about 100 µg/cc. For parenteral administration, an alternative measure of preferred amount is from about 0.001 mg/kg to about 10 mg/kg (alternatively, from about 0.01 mg/kg to about 10 mg/kg), more preferably from about 0.01 mg/kg to about 1 mg/kg (from about 0.1 mg/kg to about 1 mg/kg), will be administered. For oral administrations, an alternative measure of preferred administration amount is from about 0.001 mg/kg to about 10 mg/kg (from about 0.1 mg/kg to about 10 mg/kg), more preferably from about 0.01 mg/kg to about 1 mg/kg (from about 0.1 mg/kg to about 1 mg/kg). For administrations in suppository form, an alternative measure of preferred administration amount is from about 0.1 mg/kg to about 10 mg/kg, more preferably from about 0.1 mg/kg to about 1 mg/kg.

For use in assaying for activity in inhibiting glycine transport, eukaryotic cells, preferably QT-6 cells derived from quail fibroblasts, have been transfected to express one of the four known variants of human GlyT-1, namely GlyT-1a, GlyT-1b, GlyT-1c, or GlyT-1d, or human GlyT-2. The sequences of these GlyT-1 transporters are described in Kim et al., *Molec. Pharm.* 45: 608–617, 1994, excepting that the sequence encoding the extreme N-terminal of GlyT-1a was merely inferred from the corresponding rat-derived sequence. This N-terminal protein-encoding sequence has now been confirmed to correspond to that inferred by Kim et al. The sequence of GlyT-1d is described in U.S. Pat. No. 6,008,015, which is incorporated herein by reference in its entirety. The sequence of the human GlyT-2 is described in U.S. Pat. No. 5,919,653 which is incorporated herein by reference in its entirety. Suitable expression vectors include pRc/CMV (Invitrogen), Zap Express Vector (Stratagene Cloning Systems, LaJolla, Calif.; hereinafter "Stratagene"), pBk/CMV or pBk-RSV vectors (Stratagene), Bluescript II SK +/− Phagemid Vectors (Stratagene), LacSwitch (Stratagene), pMAM and pMAM neo (Clontech), among others. A suitable expression vector is capable of fostering expression of the included GlyT DNA in a suitable host cell, preferably a non-mammalian host cell, which can be eukaryotic, fungal, or prokaryotic. Such preferred host cells include amphibian, avian, fungal, insect, and reptilian cells.

EXAMPLES

Example 1

1-(4-Bromophenyl)prop-1-yne-3-ol (Intermediate B)

To a solution of 4-bromoiodobenzene (10.0 g, 35.3 mmol) in triethylamine ($Et_3N$, 100 mL) was added propargyl alcohol (2.7 mL, 2.57 g, 45.9 mmol), CuI (0.81 g, 4.24 mmol), and $Pd(PPh_3)_4$ (1.63 g, 1.41 mmol). The mixture was stirred overnight, then the reaction mixture was concentrated. Column chromatography (20–35% EtOAc/hexanes) provided 1-(4-bromophenyl)-1-propyne-3-ol B (6.58 g, 88%) as a yellow/orange solid. $^1$H NMR (300 MHz, $CDCl_3$) 1.77 (t, 1H), 4.48 (d, 2H), 7.29 (d, 2H), 7.45 (d, 2H).

Example 2

(Z)-1-(4-Bromophenyl)-1-iodoprop-1-ene-3-ol (Intermediate C)

A solution of 1-(4-bromophenyl)-1-propyne-3-ol B (6.58 g, 31.2 mmol) in anhydrous tetrahydrofuran (THF, 66 mL) was chilled in an ice bath. A 65% w/w solution of Red-Al in toluene (PhMe, 18.7 mL, 19.4 g, 62.4 mmol) was added dropwise over 15 minutes. After 1 hour ethyl acetate (EtOAc, 3.0 mL, 2.75 g, 31.2 mmol) was added. The reaction mixture was chilled in a dry-ice/acetone bath. A solution of $I_2$ (12.7 g, 49.9 mmol) in anhydrous THF (66 mL) was added dropwise. The reaction mixture was allowed to slowly warm to room temperature overnight. The reaction was quenched with saturated $Na_2SO_3$ and filtered through Celite. The filter cake was washed well with EtOAc. The filtrate was washed with water and brine, dried ($MgSO_4$), filtered, and concentrated. Column chromatography (20% EtOAc/hexanes) provided (Z)-1-(4-bromophenyl)-1-iodopropene-3-ol C (8.82 g, 83%) as a yellow solid. $^1$H NMR (300 MHz, $CDCl_3$) 1.82 (t, 1H), 4.37 (collapsed dd, 2H), 6.25 (t, 1H), 7.34 (d, 2H), 7.44 (d, 2H).

Example 3

(Z)-N-(1-(4-bromophenyl)-1-iodoprop-1-en-3-yl) sarcosine, $^t$butyl ester (Intermediate D)

A solution of (Z)-1-(4-bromophenyl)-1-iodopropene-3-ol C (8.81 g, 26.0 mmol) in $CH_2Cl_2$ (220 mL) was chilled in a dry-ice/acetonitrile bath under argon. $PPh_3$ (10.9 g, 41.6 mmol), and N-bromosuccinimide (NBS, 7.40 g, 41.6 mmol) were added. After 1 hour the reaction was quenched with saturated $NaHCO_3$. The mixture was washed with saturated $NaHCO_3$ and brine, dried ($Na_2SO_4$), filtered, and concentrated. The residue was immediately taken up into anhydrous acetonitrile (MeCN, 104 mL). t-butyl sarcosine hydrochloride (5.20 g, 28.6 mmol), $K_2CO_3$ (35.9 g, 260 mmol), and KI (21.6 g, 130 mmol) were added. The mixture was stirred overnight, then filtered and the filter cake washed with EtOAc. The filtrate was partitioned between EtOAc and water. The organic phase was washed with brine, dried ($MgSO_4$), filtered, and concentrated. Column chromatography (20% EtOAc/hexanes) provided (Z)-N-(1-(4-bromophenyl)-1-iodoprop-1-en-3-yl)sarcosine, $^t$butyl ester D (9.63 g, 80% over 2 steps) as a light brown oil. $^1$H NMR (300 MHz, $CDCl_3$) 1.48 (s, 9H), 2.46 (s, 3H), 3.23 (s, 2H), 3.43 (d, 2H), 6.12 (t, 1H), 7.34 (d, 2H), 7.43 (d, 2H).

Example 4-1

(Z)-N-(1-(4-bromophenyl)-1-(3-thienyl)prop-1-en-3-yl)sarcosine, $^t$butyl ester (Intermediate E(i))

To a solution of (Z)-N-(1-(4-bromophenyl)-1-iodoprop-1-en-3-yl)sarcosine, $^t$butyl ester D (29.86 g, 64.06 mmol) in dimethoxyethane (300 mL) was added 3-thiopheneboronic acid (9.02 g, 70.47 mmol), $Pd(PPh_3)_4$ (3.70 g, 3.20 mmol), and 2M $Na_2CO_3$ (300 mL). The reaction was warmed to 90° C. with vigorous mechanical stirring for 4.5 hours. The mixture was cooled, and partitioned between EtOAc and water. The organic phase was washed with brine, dried ($MgSO_4$), filtered, and concentrated. Column chromatography (2–5% acetone/hexanes) provided (Z)-N-(1-(4-bromophenyl)-1-(3-thienyl)prop-1-en-3-yl)sarcosine, $^t$butyl ester E(i) (27.06 g, 78%) as a yellow oil. $^1$H NMR (300 MHz, $CDCl_3$) 1.43 (s, 9H), 2.36 (s, 3H), 3.14 (s, 2H), 3.28 (d, 2H), 6.16 (7, 1H), 6.86 (d, 1H), 7.12–7.14 (m, 3H), 7.32 (collapsed dd, 1H), 7.41 (d, 2H).

4-2

(Z)-N-(1-(4-bromophenyl)-1-(2-thienyl)prop-1-en-3-yl)sarcosine, $^t$butyl ester (Intermediate E(ii))

In a similar fashion (Z)-N-(1-(4-bromophenyl)-1-(2-thienyl)prop-1-en-3-yl)sarcosine, $^t$butyl ester E(ii) was prepared from (Z)-N-(1-(4-bromophenyl)-1-iodoprop-1-en-3-yl)sarcosine, $^t$butyl ester D and 2-thiopheneboronic acid to provide 243 mg (52%) of a yellow oil. $^1$H NMR (300 MHz, $CDCl_3$) 1.43 (s, 9H), 2.39 (s, 3H), 3.16 (s, 2H), 3.38 (d, 2H), 6.16 (s, 1H), 6.90 (d, 1H), 7.04 (collapsed dd, 1H), 7.19 (d, 2H), 7.35 (d,1H), 7.42 (d, 2H).

4-3

(Z)-N-(1-(4-bromophenyl)-1-(3-(4-methylthienyl) prop-1-en-3-yl)sarcosine, $^t$butyl ester (Intermediate E(iii))

In a similar fashion (Z)-N-(1-(4-bromophenyl)-1-(3-(4-methylthienyl)prop-1-en-3-yl)sarcosine, $^t$butyl ester E(iii)

was prepared from (Z)-N-(1-(4-bromophenyl)-1-iodoprop-1-en-3-yl)sarcosine, ᵗbutyl ester D and 3-methyl-4-thiopheneboronic acid to provide 574 mg (61%) of a yellow oil. ¹H NMR (300 MHz, CDCl₃) 1.42 (s, 9H), 1.85 (S, 3H), 2.33 (s, 3H), 3.10–3.12 (m, 4H), 6.35 (t, 1H), 6.99 (d, 1H), 7.03(d, 1H), 7.10 (d, 2H), 7.38 (d, 2H).

4-4

(Z)-N-(1-(4-bromophenyl)-1-(2-(3-methylthienyl) prop-1-en-3-yl)sarcosine, ᵗbutyl ester (Intermediate E(iv))

In a similar fashion (Z)-N-(1-(4-bromophenyl)-1-(2-(3-methylthienyl)prop-1-en-3-yl)sarcosine, ᵗbutyl ester E(iv) was prepared from (Z)-N-(1-(4-bromophenyl)-1-iodoprop-1-en-3-yl)sarcosine, ᵗbutyl ester D and 3-methyl-2-thiopheneboronic acid to provide 436 mg (47%) of a yellow oil. ¹H NMR (300 MHz, CDCl₃) 1.43 (s, 9H), 1.97 (s, 3H), 2.35 (s, 3H), 3.12 (s, 2H), 3.16 (d, 2H), 6.43 (t, 1H), 6.90 (d, 1H) (d, 2H), 7.26 (d, 1H), 7.40 (d, 2H).

4-5

(Z)-N-(1-(4-bromophenyl)-1-(2-methylphenyl)prop-1-en-3-yl)sarcosine, ᵗbutyl ester (Intermediate E(v))

In a similar fashion (Z)-N-(1-(4-bromophenyl)-1-(2-methylphenyl)prop-1-en-3-yl)sarcosine, ᵗbutyl ester E(v) was prepared from (Z)-N-(1-(4-bromophenyl)-1-iodoprop-1-en-3-yl)sarcosine, ᵗbutyl ester D and 2-toluylboronic acid to provide 379 mg (66%) of a yellow oil.

Example 5-1

(Z)-N-(1-(4-(4-Isopropylphenyl)phenyl)-1-(3-thienyl)prop-1-en-3-yl)sarcosine, ᵗbutyl ester (Intermediate F(i))

To a solution of (Z)-N-(1-(4-bromophenyl)-1-(3-thienyl) prop-1-en-3-yl)sarcosine, ᵗbutyl ester E(i) (21.14 g, 50.05 mmol) in dimethoxyethane (210 mL) was added 4-isopropylbenzeneboronic acid (16.41 g, 100.1 mmol), Pd(PPh₃)₄ (2.89 g, 2.50 mmol), and 2M Na₂CO₃ (210 mL). The vigorously stirred mixture was heated to reflux for 2 hours. The mixture was cooled, and partitioned between EtOAc and water. The organic phase was washed with brine, dried (MgSO₄), filtered, and concentrated. Column chromatography (2–5% acetone/hexanes) followed by a second chromatography (2–20% EtOAc/hexanes) provided (Z)-N-(1-(4-(4-Isopropylphenyl)phenyl)-1-(3-thienyl)prop-1-en-3-yl)sarcosine, ᵗbutyl ester F(i) (18.65 g, 81%) as a yellow oil. ¹H NMR (300 MHz, CDCl₃) 1.29 (d, 6H), 1.44 (s, 9H), 2.39 (s, 3H), 2.95 (hept, 1H), 3.16 (s, 2H), 3.30 (d, 2H), 6.26 (t, 1H), 6.93 (d, 1H), 7.18 (d, 1H), 7.26–7.35 (m, 5H), 7.50–7.54 (m, 4H).

5-2

(Z)-N-(1-(4-(3-Thienyl)phenyl)-1-(3-thienyl)prop-1-en-3-yl)sarcosine, ᵗbutyl ester (Intermediate F(ii))

In a similar fashion (Z)-N-(1-(4-(3-Thienyl)phenyl)-1-(3-thienyl)prop-1-en-3-yl)sarcosine, ᵗbutyl ester F(ii) was prepared from (Z)-N-(1-(4-bromophenyl)-1-(3-thienyl)prop-1-en-3-yl)sarcosine, ᵗbutyl ester E(i) and 3-thiopheneboronic acid to provide 1.00 g (50%) of a yellow oil.

5-3

(Z)-N-(1-(4-(2-Thienyl)phenyl)-1-(3-thienyl)prop-1-en-3-yl)sarcosine, ᵗbutyl ester (Intermediate F(iii))

In a similar fashion (Z)-N-(1-(4-(2-Thienyl)phenyl)-1-(3-thienyl)prop-1-en-3-yl)sarcosine, ᵗbutyl ester F(iii) was prepared from (Z)-N-(1-(4-bromophenyl)-1-(3-thienyl)prop-1-en-3-yl)sarcosine, ᵗbutyl ester E(i) and 2-thiopheneboronic acid to provide 300 mg (64%) of a yellow oil.

5-4

(Z)-N-(1-(4-(2-Furyl)phenyl)-1-(3-thienyl)prop-1-en-3-yl)sarcosine, ᵗbutyl ester (Intermediate F(iv))

In a similar fashion (Z)-N-(1-(4-(2-Furyl)phenyl)-1-(3-thienyl)prop-1-en-3-yl)sarcosine, ᵗbutyl ester F(iv) was prepared from (Z)-N-(1-(4-bromophenyl)-1-(3-thienyl)prop-1-en-3-yl)sarcosine, ᵗbutyl ester E(i) and 2-furanboronic acid to provide 216 mg (82%) of a yellow oil. ¹H NMR (300 MHz, CDCl₃) 1.44 (s, 9H), 2.38 (s, 3H), 3.16 (s, 2H), 3.30 (d, 2H), 6.23 (t, 1H), 6.48 (d, 1H), 6.64 (d, 1H), 6.90 (d, 1H), 7.16 (d, 1H), 7.26–7.35 (m, 3H), 7.46 (s, 1H), 7.58 (d, 2H).

5-5

(Z)-N-(1-(4-(3-Methoxyphenyl)phenyl)-1-(3-thienyl) prop-1-en-3-yl)sarcosine, ᵗbutyl ester (Intermediate F(v))

In a similar fashion (Z)-N-(1-(4-(3-Methoxyphenyl) phenyl)-1-(3-thienyl)prop-1-en-3-yl)sarcosine, ᵗbutyl ester F(v) was prepared from (Z)-N-(1-(4-bromophenyl)-1-(3-thienyl)prop-1-en-3-yl)sarcosine, ᵗbutyl ester E(i) and 3-methoxyphenylboronic acid to provide 241 mg (99%) of a yellow oil. ¹H NMR (300 MHz, CDCl₃) 1.44 (s, 9H), 2.39 (s, 3H), 3.17 (s, 2H), 3.30 (d, 2H), 3.86 (s, 3H), 6.26 (t, 1H), 6.88–6.93 (m, 2H), 7.12 (s, 1H), 7.18–7.19 (m, 2H), 7.33–7.38 (m, 4H), 7.52 (d, 2H).

5-6

(Z)-N-(1-(4-(3-Methylphenyl)phenyl)-1-(3-thienyl) prop-1-en-3-yl)sarcosine, ᵗbutyl ester (Intermediate F(vi))

In a similar fashion (Z)-N-(1-(4-(3-Methylphenyl) phenyl)-1-(3-thienyl)prop-1-en-3-yl)sarcosine, ᵗbutyl ester F(vi) was prepared from (Z)-N-(1-(4-bromophenyl)-1-(3-thienyl)prop-1-en-3-yl)sarcosine, ᵗbutyl ester E(i) and 3-methylphenylboronic acid to provide 150 mg (64%) of a pale yellow oil. ¹H NMR (300 MHz, CDCl₃) 1.45 (s, 9H), 2.40 (s, 3H), 2.42 (s, 3H), 3.17 (s, 2H), 3.32 (d, 2H), 6.26 (t, 1H), 6.94 (d, 1H), 7.15–7.19 (m, 3H), 7.30–7.41 (m, 5H), 7.52 (d, 2H).

5-7

(Z)-N-(1-(4-(3-(Trifluoromethoxy)phenyl)phenyl)-1-(3-thienyl)prop-1-en-3-yl)sarcosine, ᵗbutyl ester (Intermediate F(vii))

In a similar fashion (Z)-N-(1-(4-(3-(Trifluoromethoxy) phenyl)phenyl)-1-(3-thienyl)prop-1-en-3-yl)sarcosine, ᵗbutyl ester F(vii) was prepared from (Z)-N-(1-(4-bromophenyl)-1-(3-thienyl)prop-1-en-3-yl)sarcosine, ᵗbutyl ester E(i) and 3-(trifluoromethoxy)phenylboronic acid to provide 127 mg (51%) of a yellow oil.

5-8

(Z)-N-(1-(4-(3-Cyanophenyl)phenyl)-1-(3-thienyl) prop-1-en-3-yl)sarcosine, ᵗbutyl ester (Intermediate F(viii))

In a similar fashion (Z)-N-(1-(4-(3-Cyanophenyl) phenyl)-1-(3-thienyl)prop-1-en-3-yl)sarcosine, ᵗbutyl ester F(viii) was prepared from (Z)-N-(1-(4-bromophenyl)-1-(3-thienyl)prop-1-en-3-yl)sarcosine, ᵗbutyl ester E(i) and 3-cyanophenylboronic acid to provide 57 mg (77%) of a yellow oil.

5-9

(Z)-N-(1-(4-(3-Thienyl)phenyl)-1-(2-thienyl)prop-1-en-3-yl)sarcosine, ᵗbutyl ester (Intermediate F(ix))

In a similar fashion (Z)-N-(1-(4-(3-Thienyl)phenyl)-1-(2-thienyl)prop-1-en-3-yl)sarcosine, ᵗbutyl ester F(ix) was prepared from (Z)-N-(1-(4-bromophenyl)-1-(2-thienyl)prop-1-en-3-yl)sarcosine, ᵗbutyl ester E(ii) and 3-thiopheneboronic acid to provide 152 mg (76%) of a yellow oil. $^1$H NMR (300 MHz, CDCl$_3$) 1.44 (s, 9H), 2.40 (s, 3H), 3.18 (s, 2H), 3.41 (d, 2H), 6.24 (t, 1H), 6.94 (d, 1H), 7.06 (dd, 1H), 7.35–7.39 (m, 4H), 7.46 (d, 1H), 7.54 (d, 2H).

5-10

(Z)-N-(1-(4-(3-Thienyl)phenyl)-1-(3-(4-methylthienyl))prop-1-en-3-yl)sarcosine, ᵗbutyl ester (Intermediate F(x))

In a similar fashion (Z)-N-(1-(4-(3-Thienyl)phenyl)-1-(3-(4-methylthienyl))prop-1-en-3-yl)sarcosine, ᵗbutyl ester F(x) was prepared from (Z)-N-(1-(4-bromophenyl)-1-(3-(4-methylthienyl)prop-1-en-3-yl)sarcosine, ᵗbutyl ester E(iii) and 3-thiopheneboronic acid to provide 222 mg (64%) of a yellow oil.

5-11

(Z)-N-(1-(4-(3-(Trifluoromethyl)phenyl)phenyl)-1-(3-(4-methylthienyl))prop-1-en-3-yl)sarcosine, ᵗbutyl ester (Intermediate F(xi))

In a similar fashion (Z)-N-(1-(4-(3-(Trifluoromethyl)phenyl)phenyl)-1-(3-(4-methylthienyl))prop-1-en-3-yl)sarcosine, ᵗbutyl ester F(xi) was prepared from (Z)-N-(1-(4-bromophenyl)-1-(3-(4-methylthienyl)prop-1-en-3-yl)sarcosine, ᵗbutyl ester E(iii) and 3-(trifluoromethyl)phenylboronic acid to provide 260 mg (54%) of a light yellow oil.

5-12

(Z)-N-(1-(4-(3-Methoxyphenyl)phenyl)-1-(3-(4-methylthienyl))prop-1-en-3-yl)sarcosine, ᵗbutyl ester (Intermediate F(xii))

In a similar fashion (Z)-N-(1-(4-(3-Methoxyphenyl)phenyl)-1-(3-(4-methylthienyl))prop-1-en-3-yl)sarcosine, ᵗbutyl ester F(xii) was prepared from (Z)-N-(1-(4-bromophenyl)-1-(3-(4-methylthienyl)prop-1-en-3-yl)sarcosine, ᵗbutyl ester E(iii) and 3-methoxyphenylboronic acid to provide 193 mg (69%) of a yellow oil.

5-13

(Z)-N-(1-(4-(3-Methylphenyl)phenyl)-1-(2-(3-methylthienyl))prop-1-en-3-yl)sarcosine, ᵗbutyl ester (Intermediate F(xiii))

In a similar fashion (Z)-N-(1-(4-(3-Methylphenyl)phenyl)-1-(2-(3-methylthienyl))prop-1-en-3-yl)sarcosine, ᵗbutyl ester F(xiii) was prepared from (Z)-N-(1-(4-bromophenyl)-1-(2-(3-methylthienyl)prop-1-en-3-yl)sarcosine, ᵗbutyl ester E(iv) and 3-methylphenylboronic acid to provide 176 mg (73%) of a yellow oil. $^1$H NMR (300 MHz, CDCl$_3$) 1.44 (s, 9H), 2.02 (s, 3H), 2.37 (s, 3H), 2.41 (s, 3H), 3.14 (s, 2H), 3.19 (d, 2H), 6.50 (t, 1H), 6.92 (d, 1H), 7.16 (d, 1H), 7.26–7.39 (m, 6H), 7.50 (d, 2H).

5-14

(Z)-N-(1-(4-(3-Thienyl)phenyl)-1-(2-methylphenyl)prop-1-en-3-yl)sarcosine, ᵗbutyl ester (Intermediate F(xiv))

In a similar fashion (Z)-N-(1-(4-(3-Thienyl)phenyl)-1-(2-methylphenyl)prop-1-en-3-yl)sarcosine, ᵗbutyl ester F(xiv) was prepared from (Z)-N-(1-(4-bromophenyl)-1-(2-methylphenyl)prop-1-en-3-yl)sarcosine, ᵗbutyl ester E(v) and 3-thiopheneboronic acid to provide 62 mg (48%) of a yellow oil.

Example 6-1

(Z)-N-(1-(4-(4-Isopropylphenyl)phenyl)-1-(3-thienyl)prop-1-en-3-yl)sarcosine (G(i))

(Z)-N-(1-(4-(4-Isopropylphenyl)phenyl)-1-(3-thienyl)prop-1-en-3-yl)sarcosine, t-butyl ester F(i) (18.62 g, 40.3 mmol) was dissolved in 96% formic acid (200 mL). The solution was warmed at 40° C. overnight, then concentrated. The residue was co-evaporated twice with CH$_2$Cl$_2$. Column chromatography (2–15% MeOH/CH$_2$Cl$_2$) provided a pale yellow solid. Trituration with methanol (MeOH) provided pure (Z)-N-(1-(4-(4-isopropylphenyl)phenyl)-1-(3-thienyl)prop-1-en-3-yl)sarcosine G(i) (11.38 g, 70%) as a white solid. $^1$H NMR (300 MHz, methanol-d$_4$) 1.23 (d, 6H), 2.47 (s, 3H), 2.92 (hept, 1H), 3.26 (s, 2H), 3.50 (d, 2H), 6.22 (t, 1H), 6.94 (d, 1H), 7.32 (d, 4H), 7.46 (d, 1H), 7.57–7.65 (m, 5H).

6-2

(Z)-N-(1-(4-(3-Thienyl)phenyl)-1-(3-thienyl)prop-1-en-3-yl)sarcosine (G(ii))

In a similar fashion (Z)-N-(1-(4-(3-thienyl)phenyl)-1-(3-thienyl)prop-1-en-3-yl)sarcosine G(ii) was prepared from (Z)-N-(1-(4-(3-thienyl)phenyl)-1-(3-thienyl)prop-1-en-3-yl)sarcosine, ᵗbutyl ester F(ii) to provide 486 mg (61%) of a white powder.

6-3

(Z)-N-(1-(4-(2-Thienyl)phenyl)-1-(3-thienyl)prop-1-en-3-yl)sarcosine (G(iii))

In a similar fashion (Z)-N-(1-(4-(2-thienyl)phenyl)-1-(3-thienyl)prop-1-en-3-yl)sarcosine G(iii) was prepared from (Z)-N-(1-(4-(2-thienyl)phenyl)-1-(3-thienyl)prop-1-en-3-yl)sarcosine, ᵗbutyl ester F(iii) to provide 145 mg (53%) of a white powder.

6-4

(Z)-N-(1-(4-(2-Furyl)phenyl)-1-(3-thienyl)prop-1-en-3-yl)sarcosine (G(iv))

In a similar fashion (Z)-N-(1-(4-(2-furyl)phenyl)-1-(3-thienyl)prop-1-en-3-yl)sarcosine G(iv) was prepared from (Z)-N-(1-(4-(2-furyl)phenyl)-1-(3-thienyl)prop-1-en-3-yl)sarcosine, ᵗbutyl ester F(iv) to provide 158 mg (97%) of a colourless oil. $^1$H NMR (300 MHz, methanol-d$_4$) 2.74 (s, 3H), 3.63 (s, 2H), 3.88 (d, 2H), 6.31 (t, 1H), 6.42 (s, 1H), 6.58 (d, 1H), 6.80 (d, 1H), 7.10 (s, 1H), 7.25 (d, 2H), 7.31 (collapsed dd, 1H), 7.41 (s, 1H), 7.52 (d, 2H).

6-5

(Z)-N-(1-(4-(3-Methoxyphenyl)phenyl)-1-(3-thienyl) prop-1-en-3-yl)sarcosine (G(v))

In a similar fashion (Z)-N-(1-(4-(3-methoxyphenyl) phenyl)-1-(3-thienyl)prop-1-en-3-yl)sarcosine G(v) was prepared from (Z)-N-(1-(4-(3-methoxyphenyl)phenyl)-1-(3-thienyl)prop-1-en-3-yl)sarcosine, $^t$butyl ester F(v) to provide 156 mg (74%) of an off-white foam. $^1$H NMR (300 MHz, methanol-$d_4$) 2.76 (s, 3H), 3.56 (s, 2H), 3.82 (s, 3H), 3.91 (d, 2H), 6.36 (t, 1H), 6.82–6.88 (m, 2H), 7.06–7.11 (m, 3H), 7.26–7.32 (m, 4), 7.46 (d, 2H).

6-6

(Z)-N-(1-(4-(3-Methylphenyl)phenyl)-1-(3-thienyl) prop-1-en-3-yl)sarcosine (G(vi))

In a similar fashion (Z)-N-(1-(4-(3-methylphenyl) phenyl)-1-(3-thienyl)prop-1-en-3-yl)sarcosine G(vi) was prepared from (Z)-N-(1-(4-(3-methylphenyl)phenyl)-1-(3-thienyl)prop-1-en-3-yl)sarcosine, $^t$butyl ester F(vi) to provide 127 mg (100%) of a colourless oil. $^1$H NMR (300 MHz, methanol-$d_4$) 2.38 (s, 3H), 2.76 (s, 3H), 3.56 (s, 2H), 3.90 (d, 2H), 6.36 (t, 1H), 6.83 (d, 1H), 7.10–7.15 (m, 2H), 7.24–7.33 (m, 6H), 7.46 (d, 2H).

6-7

(Z)-N-(1-(4-(3-(Trifluoromethoxy)phenyl)phenyl)-1-(3-thienyl)prop-1-en-3-yl)sarcosine (G(vii))

In a similar fashion (Z)-N-(1-(4-(3-(trifluoromethoxy) phenyl)phenyl)-1-(3-thienyl)prop-1-en-3-yl)sarcosine G(vii) was prepared from (Z)-N-(1-(4-(3-(trifluoromethoxy) phenyl)phenyl)-1-(3-thienyl)prop-1-en-3-yl)sarcosine, $^t$butyl ester F(vii) to provide 80 mg (78%) of a white powder.

6-8

(Z)-N-(1-(4-(3-Cyanophenyl)phenyl)-1-(3-thienyl) prop-1-en-3-yl)sarcosine (G(viii))

In a similar fashion (Z)-N-(1-(4-(3-cyanophenyl)phenyl)-1-(3-thienyl)prop-1-en-3-yl)sarcosine G(viii) was is prepared from (Z)-N-(1-(4-(3-cyanophenyl)phenyl)-1-(3-thienyl)prop-1-en-3-yl)sarcosine, $^t$butyl ester F(viii) to provide 48 mg (84%) of a white powder.

6-9

(Z)-N-(1-(4-(3-Thienyl)phenyl)-1-(2-thienyl)prop-1-en-3-yl)sarcosine (G(ix))

In a similar fashion (Z)-N-(1-(4-(3-thienyl)phenyl)-1-(2-thienyl)prop-1-en-3-yl)sarcosine G(ix) was prepared from (Z)-N-(1-(4-(3-thienyl)phenyl)-1-(2-thienyl)prop-1-en-3-yl) sarcosine, $^t$butyl ester F(ix) to provide 108 mg (59%) of a white powder. $^1$H NMR (300 MHz, CDCl$_3$) 2.73 (s, 3H), 3.44 (s, 2H), 3.88 (d, 2H), 6.14 (t, 1H), 6.90 (d, 1H), 7.04 (dd, 1H), 7.26–7.34 (m, 4H), 7.38–7.41 (m, 2H), 7.48 (d, 2H).

6-10

(Z)-N-(1-(4-(3-Thienyl)phenyl)-1-(3-(4-methylthienyl))prop-1-en-3-yl)sarcosine (G(x))

In a similar fashion (Z)-N-(1-(4-(3-thienyl)phenyl)-1-(3-(4-methylthienyl))prop-1-en-3-yl)sarcosine G(x) was prepared from (Z)-N-(1-(4-(3-thienyl)phenyl)-1-(3-(4-methylthienyl))prop-1-en-3-yl)sarcosine, $^t$butyl ester F(x) to provide 157 mg (82%) of a white powder.

6-11

(Z)-N-(1-(4-(3-(Trifluoromethyl)phenyl)phenyl)-1-(3-(4-methylthienyl))prop-1-en-3-yl)sarcosine (G(xi))

In a similar fashion (Z)-N-(1-(4-(3-(trifluoromethyl) phenyl)phenyl)-1-(3-(4-methylthienyl))prop-1-en-3-yl) sarcosine G(xi) was prepared from (Z)-N-(1-(4-(3-(trifluoromethyl)phenyl)phenyl)-1-(3-(4-methylthienyl)) prop-1-en-3-yl)sarcosine, $^t$butyl ester F(xi) to provide 99 mg (73%) of a white powder.

6-12

(Z)-N-(1-(4-(3-Methoxyphenyl)phenyl)-1-(3-(4-methylthienyl))prop-1-en-3-yl)sarcosine (G(xii))

In a similar fashion (Z)-N-(1-(4-(3-methoxyphenyl) phenyl)-1-(3-(4-methylthienyl))prop-1-en-3-yl)sarcosine G(xii) was prepared from (Z)-N-(1-(4-(3-methoxyphenyl) phenyl)-1-(3-(4-methylthienyl))prop-1-en-3-yl)sarcosine, $^t$butyl ester F(xii) to provide 152 mg (69%) of a white powder.

6-13

(Z)-N-(1-(4-(3-Methylphenyl)phenyl)-1-(2-(3-methylthienyl))prop-1-en-3-yl)sarcosine (G(xiii))

In a similar fashion (Z)-N-(1-(4-(3-methylphenyl) phenyl)-1-(2-(3-methylthienyl))prop-1-en-3-yl)sarcosine G(xiii) was prepared from (Z)-N-(1-(4-(3-methylphenyl) phenyl)-1-(2-(3-methylthienyl))prop-1-en-3-yl)sarcosine, $^t$butyl ester F(xiii) to provide 129 mg (99%) of a white powder. $^1$H NMR (300 MHz, methanol-$d_4$) 1.97 (s, 3H), 2.38 (s, 3H), 2.80 (s, 3H), 3.58 (s, 2H), 3.81 (d, 2H), 6.65 (t, 1H), 6.90 (d, 1H) (collapsed dd, 1H), 7.26–7.38 (m, 6H), 7.48 (d, 2H).

6-14

(Z)-N-(1-(4-(3-Thienyl)phenyl)-1-(2-methylphenyl) prop-1-en-3-yl)sarcosine (G(xiv))

In a similar fashion (Z)-N-(1-(4-(3-thienyl)phenyl)-1-(2-methylphenyl)prop-1-en-3-yl)sarcosine G(xiv) was prepared from (Z)-N-(1-(4-(3-thienyl)phenyl)-1-(2-methylphenyl)prop-1-en-3-yl)sarcosine, $^t$butyl ester F(xiv) to provide 37 mg (61%) of a white powder.

Example 7

Assay of Transport via GlyT-1

This example illustrates a method for the measurement of glycine uptake by transfected cultured cells.

Cells stably transfected with GlyT-1 C (see Kim, et al., *Molecular Pharmacology*, 45, 1994:608–617) were washed twice with HEPES buffered saline (HBS). The cells were then incubated for 10 minutes at 37° C. with either (a) no potential competitor, (b) 10 mM non-radioactive glycine or (c) a concentration of a candidate drug. A range of concentrations of the candidate drug was used to generate data for calculating the concentration resulting in 50% of the effect (e.g., the $IC_{50}$s, which are the concentrations of drug inhibiting glycine uptake by 50%). A solution was then added containing [³H]glycine at a final concentration of 50 nM (17.5 Ci/mmol). The cells were then incubated with gentle shaking for another 30 minutes at 37° C., after which the reaction mixture was aspirated and washed three times with ice-cold HBS. The cells were lysed with scintillant and allowed to equilibrate. The radioactivity in the cells was determined using a scintillation counter. Data was compared between the same cells contacted or not contacted by a candidate agent, depending on the assay being conducted.

The compounds of the present invention were active as GlyT-1 inhibitors.

Example 8

Assay of Binding to NMDA Receptors-associated Glycine Binding Site

This example illustrates a method used to measure the interaction of compounds to the glycine site on the NMDA receptor. In this assay a known NMDA glycine site binding agent, (tritiated-MDL 105519, available from Amersham), is used to bind to rat hippocampal tissue. The test compound is then introduced and allowed to displace the hot ligand. Binding of the test compound will displace the hot ligand and result in reduced radioactivity, which can be quantified. Compounds are generally tested at two concentrations if inhibition is observed the compounds are retested at several concentrations to generate a dose response curve from which an IC50 may be determined.

The test compounds are prepared for the assay by diluting with 50 mM Tris Acetate buffer. Rat hippocampal membrane aliquots used in the assay are washed twice with cold 10 mM Tris Acetate buffer and subjected to ultracentrifugation at 20,000 rpm for 15 minutes, and rehomogenization between washes. The final pellets are then resuspended in 50 mM Tris Acetate buffer to provide the membranes at a concentration appropriate to the assay. Non-specific binding is defined in the presence of 1 mM glycine. Total binding is defined by the presence of Tris acetate buffer only.

The reaction mixture is prepared by combining 75 µg of homogenized hippocampal membrane preparation with [3H]-MDL 105519 to a final concentration of 5 nM and glycine or test compound as a solution in Tris Acetate Buffer. The reaction is shaken while incubating at room temp for 30 minutes. The plates are then harvested onto GFC filters using a 48 w Brandell Harvestor. The GFC filters are pre-treated for at least 30 minutes with a solution of 0.5% BSA made in distilled water to reduce non-specific binding of the hot ligand to the filter. The plate wells are washed with 4–5 volumes of cold 50 mM Tris Acetate buffer. The filters are then transferred to scintillation vials and 2 mls of scintillant is added to each vial. The vials are allowed to sit overnight before being counted in a Beckman β-counter. The data is analyzed using Prism software.

The compounds of the present invention show no significant binding to the NMDA receptor-associated glycine binding site.

Example 9

Glycine Receptor Binding Assay

This example illustrates an assay used to measure cross reactivity of the compounds with the Glycine receptor. In this assay the known glycine receptor binding agent, [3H]-Strychnine is used to bind to rat spinal cord tissue. The test compound is then introduced and allowed to displace the hot ligand. Binding of the test compound will displace the hot ligand and result in reduced radioactivity, which can be quantified. Compounds are generally tested at two concentrations, if inhibition is observed the compounds are retested at several concentrations to generate a dose response curve from which an IC50 may be determined.

The test compounds are prepared for the assay by diluting in potassium phosphate buffer. The aliquots of rat spinal cord membrane used in the assay are washed with two portions of cold Phosphate buffer followed by microcentrifugation at 4° C., at 14,000 rpm between washings. The final pellets are then resuspended in a volume of phosphate buffer to provide concentrations appropriate to the assay conditions. The non-specific and total binding are defined by 10 mM final concentration of glycine and phosphate buffer only, respectively.

The reaction mixture is prepared by combining 150 µg of the rat spinal cord membrane with [3H]-strychnine to a final concentration of 7 nM and glycine or test compound. The reaction mixture is incubated for two hours while shaking on ice. The plates are then harvested onto GFC filters using a 48 w Brandall Harvestor. The GFC filter is pretreated for at least 30 minutes with a solution of 0.5% BSA made is distilled water to reduce non-specific binding. The plate wells are washed with 4–5 volumes of cold phosphate buffer. The filters are then transferred to scintillation vials and 2 mls of scintillant is added to each vial. The vials are allowed to sit overnight before being counted in a Beckman β-counter. The data is analyzed using Prism software.

The compounds of the present invention show no significant binding to the glycine receptor.

Example 10

Assay to Measure Toxicity in Mice

This example illustrated a 5 day chronic oral dosing toxicity study with GlyT1 inhibitors. Compounds were administered orally (PO) to male CD-1 mice for 5 days, at 40 mg/kg/day. Behavioral observations (clinical signs) and body weights were recorded daily for all compounds tested. Male CD-1 mice were purchased from Charles River Labs (Kingston, N.Y.). The animals weighed between 20–25 grams upon arrival. Animals were acclimatized in a temperature/humidity (72° ±5° F./50%±5%) controlled vivarium, with a common 12 hour light/dark cycle (Lights on 0700 hrs) for 5 days prior to test. All animals were allowed food (Purina Labdiete® Rodent chow # 5001) and water (supplied by Elizabethtown Water Company) ad libitum during the acclimation period and throughout the study. On the day prior to test initiation animals were randomly assigned to groups: All animals chosen for test weighed at least 20 grams and appeared in good condition. Each animal was dosed once daily for 5 days. Animals remained on site for a 3 day recovery period following the chronic dosing period.

A stock concentration of each test compound was prepared fresh on the day of study initiation. Aliquots were diluted to the needed concentrations for daily dosing. Stock solutions were kept in a refrigerator when not in use. Each compound was dissolved in a small amount of distilled water. One equivalent of sodium hydroxide (2 N) may have been added to aid in dissolution of each test agent. Vehicle was then added quantum sufficiat to give the final volume. Final volumes were adjusted to reflect percent free base when appropriate. The vehicle used in this experiment was Hydroxypropyl-β-cyclodextrine (HPCD) Acros, lot 011849601, dissolved in distilled water to form a 10% weight/volume concentration. The pH was adjusted, using sodium hydroxide (2 N), to equal that of the test agents (usually between 8 to 10). All prepared test compounds were either in solution, and clear, or in suspension, and slightly cloudy. Suspensions were mixed immediately prior to use.

All animals were administered either test compound or vehicle Per Os (PO) via 21 gauge gavage needles, in volumes of 10.0 ml/kg. Daily body weights were used to determine individual dosing volumes. All test compounds were weighed on a Denver Instruments analytical balance (model # A-250). Animals were weighed on a top loading Ohaus portable balance model # LS2000.

Animals were assessed for overt behaviors (clinical signs) immediately following administration of test agents, then again at 4 and 24 hours. Animals were assessed for 27 separate clinical signs:

Activity: Describe if the animal is abnormally hyper- or hypo-active.
Ataxia: Unsteady gait, inability to coordinate voluntary muscular movements.
Catalepsy: A condition characterized by waxy rigidity of the limbs, which may be placed in various positions that are maintained for a time, lack of response to stimuli, show pulse and respiration, and pale skin.
Chromaturia: A reddish discharge in the urine.
Chromodacryorrhea: A reddish discharge from the eyes.
Condition of Stool: Soft and watery, hard and small.
Convulsions:
  Clonic: A generalized intermittent tonus and relaxation of the skeletal muscles.
  Tonic: A generalized constant muscular tonus, often accompanied by hind and/or fore limb extension.
Cyanosis: A bluish color of external tissues (ears, toes, tail).
Death: Clarify whether of a spontaneous nature, or euthanization.
Enophthalmia: Abnormal retraction of the eyes into the orbits.
Epistaxis: A reddish discharge from the nose.
Exophthalmia: Abnormal protrusion of the eyes.
Flaccidity: Skeletal muscles appear to be without tone.
Hunched Posture: The animal appears to be walking high up off the ground.
Hypersensitive to Touch: The animal vocalizes, or becomes excessively active during handling.
Lacrimation (both eyes): Secretion and discharge of tears.
Lateral Recumbency: Animal is spontaneously supine.
Loss of Righting: Animal remains supine when placed in that position.
Miosis: Excessive contraction of the pupils of the eye.
Mydriasis: Excessive dilation of the pupils of the eye.
Palpabral Ptosis: Refers to the drooping of the upper eyelid of both eyes.
Piloerection: Bristling of the fur on the back and neck.
Rales (wet or dry): Wet (mucousal): a bubbling sound heard during respiration.
Dry: harsh or musical sound heard during respiration.
Respiration (↑↓): An unusual increase or decrease in this activity.
Rigidity:
  Waxy: The extremities stay in the position in which they are placed.
  Lead pipe: muscular rigor, the extremities are difficult to move.
Salivation (Increased): The formation and excessive secretion of saliva.
Sedation: The animal responds slowly when touched or handled.
Stereotypy: Constant repetition of certain meaningless movements.
Tremors:
  Fine: a constant fast vibration of the body and/or extremities.
  Coarse: a fast vibration of the body and/or extremities that seems to increase and decrease with time.

Any animal that exhibited 1) loss of body weight, such that it's value dropped to 75% of the control group's mean value for 2 consecutive days, or 2) onset of a moribund condition, such that the animal could no longer feed or drink normally, were sacrificed prior to study conclusion.

Toxicity data obtained through the assay as described above is provided in Tables 1 to 14 for Compounds Gi to Gxiv inclusive. The animals were observed immediately following administration and again at 4 hours and 24 hours. Observations are reported using the code number from the following chart:

| 0 Appeared Normal | 7 Epistaxis | 14 Palpabral Ptosis | 21 Rigidity |
|---|---|---|---|
| 1 Activity (inc./dec.) | 8 Cyanosis | 15 Loss of Righting | 22 Ataxia |
| 2 Sedation/Lethargy | 9 Flaccidity | 16 Chromaturia | 23 Tremors |
| 3 Piloerection | 10 Respiration | 17 Salivation | 24 Convulsions |
| 4 Stereotypy | 11 Hunched Posture | 18 Lacrimation | 25 Catalepsy |
| 5 Soft Stool | 12 Enophthalmia | 19 Miosis | 26 Lateral Recumbency |
| 6 Chromodacryorrhea | 13 Exophthalmia | 20 Mydriasis | 27 Death |

TABLE 1

Compound G(iii)

| Animal # | Dose (mg/kg) | Day 1 | Day 2 | Day 3 | Day 4 | Day 5 |
|---|---|---|---|---|---|---|
| | | | 4 hours | | | |
| 1 | 40 | 0 | 0 | 0 | 14 | 0 |
| 2 | 40 | 0 | 0 | 0 | 0 | 0 |
| 3 | 40 | 0 | 0 | 0 | 14, 10 | 0 |
| | | | 24 hours | | | |
| 1 | 40 | 0 | 0 | 0 | 0 | 0 |
| 2 | 40 | 0 | 0 | 0 | 0 | 0 |
| 3 | 40 | 0 | 0 | 0 | 0 | 0 |

TABLE 2

Compound G(viii)

| Animal # | Dose (mg/kg) | 1 | 2 | 3 | 4 | 5 |
|---|---|---|---|---|---|---|
| | | | | 4 hours | | |
| 1 | 40 | 0 | 0 | 0 | 0 | 0 |
| 2 | 40 | 0 | 0 | 0 | 0 | 0 |
| 3 | 40 | 0 | 0 | 0 | 0 | 0 |
| | | | | 24 hours | | |
| 1 | 40 | 0 | 0 | 0 | 0 | 0 |
| 2 | 40 | 0 | 0 | 0 | 0 | 0 |
| 3 | 40 | 0 | 0 | 0 | 0 | 0 |

TABLE 3

Compound G(xiv)

| Animal # | Dose (mg/kg) | 1 | 2 | 3 | 4 | 5 |
|---|---|---|---|---|---|---|
| | | | | 4 hours | | |
| 1 | 40 | 0 | 0 | 0 | 0 | 0 |
| 2 | 40 | 0 | 0 | 0 | 0 | 0 |
| 3 | 40 | 0 | 0 | 0 | 0 | 0 |
| | | | | 24 hours | | |
| 1 | 40 | 0 | 0 | 0 | 0 | 0 |
| 2 | 40 | 0 | 0 | 0 | 0 | 0 |
| 3 | 40 | 0 | 0 | 0 | 0 | 0 |

TABLE 4

Compound G(ix)

| Animal # | Dose (mg/kg) | 1 | 2 | 3 | 4 | 5 |
|---|---|---|---|---|---|---|
| | | | | 4 hours | | |
| 1 | 40 | 0 | 0 | 0 | 0 | 0 |
| 2 | 40 | 0 | 0 | 0 | 0 | 0 |
| 3 | 40 | 0 | 0 | 0 | 0 | 0 |
| | | | | 24 hours | | |
| 1 | 40 | 0 | 0 | 0 | 0 | 0 |
| 2 | 40 | 0 | 0 | 0 | 0 | 0 |
| 3 | 40 | 0 | 0 | 0 | 0 | 0 |

TABLE 5

Compound G(ii)

| Animal # | Dose (mg/kg) | 1 | 2 | 3 | 4 | 5 |
|---|---|---|---|---|---|---|
| | | | | 4 hours | | |
| 1 | 40 | 0 | 1 | 0 | 1, 22, 26, 15 | 1, H |
| 2 | 40 | 0 | 0 | 0 | 1, 22, 24+, 26, 1 | 1, 22, 15, |

TABLE 5-continued

Compound G(ii)

| Animal # | Dose (mg/kg) | 1 | 2 | 3 | 4 | 5 |
|---|---|---|---|---|---|---|
| 3 | 40 | 0 | 0 | 0 | 5, 14 0 | 14 0 |
| | | | | 24 hours | | |
| 1 | 40 | 0 | 0 | 0 | 0 | 0 |
| 2 | 40 | 0 | 0 | 0 | 0 | 0 |
| 3 | 40 | 0 | 0 | 0 | 0 | 0 |

H-Head Butting
+touch-evoked

TABLE 6

Compound G(x)

| Animal # | Dose (mg/kg) | 1 | 2 | 3 | 4 | 5 |
|---|---|---|---|---|---|---|
| | | | | 4 hours | | |
| 1 | 40 | 0 | 0 | 0 | 0 | 0 |
| 2 | 40 | 0 | 0 | 0 | 0 | 0 |
| 3 | 40 | 0 | 0 | 0 | 0 | 0 |
| | | | | 24 hours | | |
| 1 | 40 | 0 | 0 | 0 | 0 | — |
| 2 | 40 | 0 | 0 | 0 | 0 | — |
| 3 | 40 | 0 | 0 | 0 | 0 | — |

TABLE 7

Compound G(xii)

| Animal # | Dose (mg/kg) | 1 | 2 | 3 | 4 | 5 |
|---|---|---|---|---|---|---|
| | | | | 4 hours | | |
| 1 | 40 | 0 | 0 | 0 | 0 | 0 |
| 2 | 40 | 0 | 0 | 0 | 0 | 0 |
| 3 | 40 | 0 | 0 | 0 | 0 | 0 |
| | | | | 24 hours | | |
| 1 | 40 | 0 | 0 | 0 | 0 | — |
| 2 | 40 | 0 | 0 | 0 | 0 | — |
| 3 | 40 | 0 | 0 | 0 | 0 | — |

TABLE 8

Compound G(xi)

| Animal # | Dose (mg/kg) | 1 | 2 | 3 | 4 | 5 |
|---|---|---|---|---|---|---|
| | | | | 4 hours | | |
| 1 | 40 | 0 | 0 | 0 | 0 | 0 |
| 2 | 40 | 0 | 0 | 0 | 0 | 0 |
| 3 | 40 | 0 | 0 | 0 | 0 | 0 |

TABLE 8-continued

Compound G(xi)

| Animal # | Dose (mg/kg) | Day | | | | |
|---|---|---|---|---|---|---|
| | | 1 | 2 | 3 | 4 | 5 |
| 24 hours | | | | | | |
| 1 | 40 | 0 | 0 | 0 | 0 | — |
| 2 | 40 | 0 | 0 | 0 | 0 | — |
| 3 | 40 | 0 | 0 | 0 | 0 | — |

TABLE 9

Compound G(xiii)

| Animal # | Dose (mg/kg) | Day | | | | |
|---|---|---|---|---|---|---|
| | | 1 | 2 | 3 | 4 | 5 |
| 4 hours | | | | | | |
| 1 | 40 | 0 | 0 | 0 | 0 | 0 |
| 2 | 40 | 0 | 0 | 0 | 0 | 0 |
| 3 | 40 | 0 | 0 | 0 | 0 | 0 |
| 24 hours | | | | | | |
| 1 | 40 | 0 | 0 | 0 | 0 | — |
| 2 | 40 | 0 | 0 | 0 | 0 | — |
| 3 | 40 | 0 | 0 | 0 | 0 | — |

TABLE 10

Compound G(i)

| Animal # | Dose (mg/kg) | Day | | | | |
|---|---|---|---|---|---|---|
| | | 1 | 2 | 3 | 4 | 5 |
| 4 hours | | | | | | |
| 1 | 40 | 0 | 0 | 0 | 0 | 0 |
| 2 | 40 | 0 | 0 | 0 | 0 | 0 |
| 3 | 40 | 0 | 0 | 0 | 0 | 0 |
| 24 hours | | | | | | |
| 1 | 40 | 0 | 0 | 0 | 0 | 0 |
| 2 | 40 | 0 | 0 | 0 | 0 | 0 |
| 3 | 40 | 0 | 0 | 0 | 0 | 0 |

TABLE 11

Compound G(v)

| Animal # | Dose (mg/kg) | Day | | | | |
|---|---|---|---|---|---|---|
| | | 1 | 2 | 3 | 4 | 5 |
| 4 hours | | | | | | |
| 1 | 40 | 0 | 0 | 0 | 0 | 0 |
| 2 | 40 | 0 | 0 | 0 | 0 | 0 |
| 3 | 40 | 0 | 0 | 0 | 0 | 0 |
| 24 hours | | | | | | |
| 1 | 40 | 0 | 0 | 0 | 0 | 0 |
| 2 | 40 | 0 | 0 | 0 | 0 | 0 |
| 3 | 40 | 0 | 0 | 0 | 0 | 0 |

TABLE 12

Compound G(vi)

| Animal # | Dose (mg/kg) | Day | | | | |
|---|---|---|---|---|---|---|
| | | 1 | 2 | 3 | 4 | 5 |
| 4 hours | | | | | | |
| 1 | 40 | 0 | 0 | 0 | 0 | 0 |
| 2 | 40 | 0 | 0 | 0 | 0 | 0 |
| 3 | 40 | 0 | 0 | 0 | 0 | 0 |
| 24 hours | | | | | | |
| 1 | 40 | 0 | 0 | 0 | 0 | 0 |
| 2 | 40 | 0 | 0 | 0 | 0 | 0 |
| 3 | 40 | 0 | 0 | 0 | 0 | 0 |

TABLE 13

Compound G(vii)

| Animal # | Dose (mg/kg) | Day | | | | |
|---|---|---|---|---|---|---|
| | | 1 | 2 | 3 | 4 | 5 |
| 4 hours | | | | | | |
| 1 | 40 | 0 | 0 | 0 | 0 | 0 |
| 2 | 40 | 0 | 0 | 0 | 0 | 0 |
| 3 | 40 | 0 | 0 | 0 | 0 | 0 |
| 24 hours | | | | | | |
| 1 | 40 | 0 | 0 | 0 | 0 | 0 |
| 2 | 40 | 0 | 0 | 0 | 0 | 0 |
| 3 | 40 | 0 | 0 | 0 | 0 | 0 |

TABLE 14

Compound G(iv)

| Animal # | Dose (mg/kg) | Day | | | | |
|---|---|---|---|---|---|---|
| | | 1 | 2 | 3 | 4 | 5 |
| 4 hours | | | | | | |
| 1 | 40 | 14 | 0 | 14 | 0 | 14 |
| 2 | 40 | 1, 22, 14, 10, 2 | 1, 22, 15, 10 | 0 | 1, 22, 14, H, 10, 2 | 0 |
| 3 | 40 | 0 | 0 | 14 | 0 | 0 |

TABLE 14-continued

| | | Compound G(iv) | | | | |
|---|---|---|---|---|---|---|
| Animal # | Dose (mg/kg) | Day | | | | |
| | | 1 | 2 | 3 | 4 | 5 |
| | | 24 hours | | | | |
| 1 | 40 | 0 | 0 | 0 | 0 | 0 |
| 2 | 40 | 0 | 0 | 0 | 0 | 0 |
| 3 | 40 | 0 | 0 | 0 | 0 | 0 |

H-Head Butting

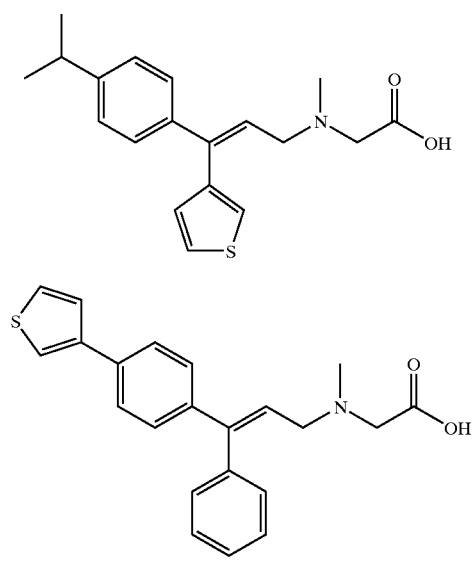

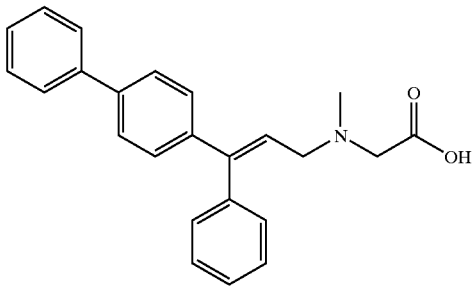

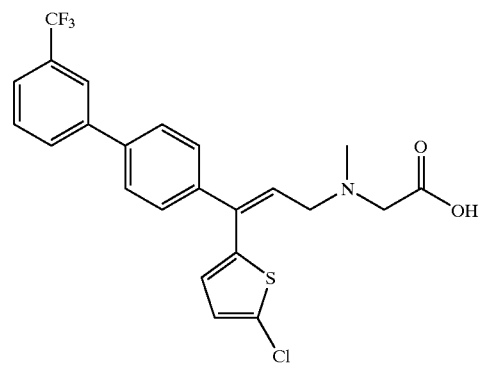

By way of comparison the compounds of formula 1 are less toxic than other GlyT1 inhibitors of similar potency. For example compounds H, I, J, and K below, show a higher toxicity profile than the compounds of the present invention as seen in tables 15, 16, 17, and 18.

TABLE 15

| | | Compound H* | | | | |
|---|---|---|---|---|---|---|
| Animal # | Dose (mg/kg) | Day | | | | |
| | | 1 | 2 | 3 | 4 | 5 |
| 1 | 40 | 0 | 0 | 0 | 1, 22, 8, 14, 10, 2 | 1, 2 |
| 2 | 40 | 0 | 1, 22, 10, 2 | 1, 26, 15, 3, 10, 2 | 0 | 1, 2 |
| 3 | 40 | 1, 3, 14, 2 | 1, 22, 14, 2 | 1, 22, 9, 10, 2 | 1, 9, 26, 15, 14, 10, 2 | 1, 2 |

*In this experiment behavioral observations were only recorded once per day.

TABLE 16

| | | Compound I | | | | |
|---|---|---|---|---|---|---|
| Animal # | Dose (mg/kg) | Day | | | | |
| | | 1 | 2 | 3 | 4 | 5 |
| | | 4 hours | | | | |
| 16 | 40 | ↓1, 26, ↓10 | ↓1, 22, 26, ↓10 | ↓1, 22, ↓10 | ↓1, 22, 26, ↓10, I | ↓1, 22, ↓10 |
| 17 | 40 | ↓1, 22, ↓10 | ↓1, 22, ↓10 | ↓1, 26, ↓10 | ↓1, 26, 15, ↓10 | ↓1, 26, ↓10 |

TABLE 16-continued

Compound I

| Animal # | Dose (mg/kg) | Day 1 | Day 2 | Day 3 | Day 4 | Day 5 |
|---|---|---|---|---|---|---|
| 18 | 40 | ↓1, 22, 26, ↓10 | ↓1, 22, ↓10 | ↓1, 22, 26, ↓10 | ↓1, 22, ↓10 | ↓1, 22, ↓10 |

24 hours

| 16 | 40 | 0 | 0 | 0 | 0 | — |
| 17 | 40 | 0 | 0 | 0 | 0 | — |
| 18 | 40 | 0 | 0 | 0 | 0 | — |

I = severe itching

TABLE 17

Compound J

| Animal # | Dose (m↓kg) | Day 1 | Day 2 | Day 3 | Day 4 | Day 5 |
|---|---|---|---|---|---|---|

4 hours

| 1 | 10 | 0 | 0 | 0 | 0 | 0 |
| 2 | 10 | 0 | 0 | 0 | 0 | 0 |
| 3 | 10 | 0 | 0 | 0 | 0 | 0 |

24 hours

| 1 | 25 | 0 | 1, 2 | 1, 9, 18, 26, 15, 14, 10, 2* | — | — |
| 2 | 25 | 0 | 0 | 1, 6, 9, 18, 26, 15, 14, 10, 2* | — | — |
| 3 | 25 | 0 | 2 | 1, 9, 18, 26, 15, 14, 10, 2, 23* | — | — |

TABLE 18

Compound K

| Animal # | Dose (mg/kg) | Day 1 | Day 2 | Day 3 | Day 4 | Day 5 |
|---|---|---|---|---|---|---|

4 hours

| 1 | 40 | 1 | — | — | — | — |
| 2 | 40 | 0 | — | — | — | — |
| 3 | 40 | 0 | 1, 22, 24, 15, 2 | — | — | — |

24 hours

| 1 | 40 | 1, 22, 18, 26, 15, 14, 10, 23, 27* | — | — | — | — |
| 2 | 40 | 1, 26, 15, 14, 10, 27* | — | — | — | — |
| 3 | 40 | 1, 26 | 1, 22, 24, 15, 14, 10, 23, 27* | — | — | — |

*Animal was euthanized due to a moribund condition

We claim:
1. A compound of formula 1

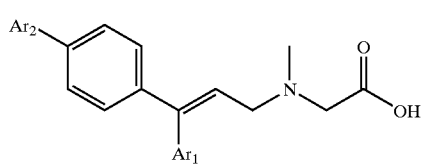

Formula I wherein:
Ar$_1$ is a thiophene group which may be 2 or 3 thiophene and is optionally substituted with up to one substituent selected from methyl or ethyl;
Ar$_2$ is selected from thiophene, furan and substituted phenyl, wherein the substituent on the phenyl group is selected from C$_{1-6}$ alkyl, halo, C$_{1-6}$ haloalkyl, C$_{1-6}$ alkoxy, C$_{1-6}$ haloalkoxy, cyano
and a salt, solvate and hydrate thereof.

2. A compound according to claim 1 wherein Ar$_1$ is 2-thiophene.
3. A compound according to claim 1 wherein Ar$_1$ is 2-(3-methylthiophene).
4. A compound according to claim 1 wherein Ar$_1$ is 3-thiophene.
5. A compound according to claim 1 wherein Ar$_1$ is 3-(4-methylthiophene).
6. A compound according to claim 1 wherein Ar$_2$ is substituted phenyl where the substituent is selected from CF$_3$, Me, iPr, MeO, CN, and CF$_3$O.
7. A compound according to claim 1 wherein Ar$_2$ is furan.
8. A compound according to claim 1 wherein Ar$_2$ is thiophene.
9. A compound according to claim 1 selected from the group consisting of:
(Z)-N-(1-(4-(4-Isopropylphenyl)phenyl)-1-(3-thienyl)prop-1-en-3-yl)sarcosine;
(Z)-N-(1-(4-(3-Thienyl)phenyl)-1-(3-thienyl)prop-1-en-3-yl)sarcosine;
(Z)-N-(1-(4-(2-Thienyl)phenyl)-1-(3-thienyl)prop-1-en-3-yl)sarcosine;
(Z)-N-(1-(4-(2-Furyl)phenyl)-1-(3-thienyl)prop-1-en-3-yl)sarcosine;
(Z)-N-(1-(4-(3-Methoxyphenyl)phenyl)-1-(3-thienyl)prop-1-en-3-yl)sarcosine;
(Z)-N-(1-(4-(3-Methylphenyl)phenyl)-1-(3-thienyl)prop-1-en-3-yl)sarcosine;
(Z)-N-(1-(4-(3-(Trifluoromethoxy)phenyl)phenyl)-1-(3-thienyl)prop-1-en-3-yl)sarcosine;
(Z)-N-(1-(4-(3-Cyanophenyl)phenyl)-1-(3-thienyl)prop-1-en-3-yl)sarcosine;

(Z)-N-(1-(4-(3-Thienyl)phenyl)-1-(2-thienyl)prop-1-en-3-yl)sarcosine;

(Z)-N-(1-(4-(3-Thienyl)phenyl)-1-(3-(4-methylthienyl))prop-1-en-3-yl)sarcosine;

(Z)-N-(1-(4-(3-(Trifluoromethyl)phenyl)phenyl)-1-(3-(4-methylthienyl))prop-1-en-3-yl)sarcosine;

(Z)-N-(1-(4-(3-Methoxyphenyl)phenyl)-1-(3-(4-methylthienyl))prop-1-en-3-yl)sarcosine; and (Z)-N-(1-(4-(3-Methylphenyl)phenyl)-1-(2-(3-methylthienyl))prop-1-en-3-yl)sarcosine.

10. The compound (Z)-N-(1-(4-(3-Thienyl)phenyl)-1-(2-methylphenyl)prop-1-en-3-yl)sarcosine.

11. The compound of claim 9, (Z)-N-(1-(4-(2-Furyl)phenyl)-1-(3-thienyl)prop-1-en-3-yl)sarcosine.

12. The compound of claim 9, (Z)-N-(1-(4-(4-Isopropylphenyl)phenyl)-1-(3-thienyl)prop-1-en-3-yl)sarcosine.

13. A composition comprising a compound of claim 1 and a carrier.

14. A composition comprising a compound of claim 10 and a carrier.

15. A composition comprising a compound of claim 11 and a carrier.

16. A composition comprising a compound of claim 12 and a carrier.

17. A pharmaceutical composition comprising a therapeutically effective amount of a compound of claim 1 and a pharmaceutically acceptable carrier.

18. A pharmaceutical composition comprising a therapeutically effective amount of a compound of claim 10 and a pharmaceutically acceptable carrier.

19. A pharmaceutical composition comprising a therapeutically effective amount of a compound of claim 11 and a pharmaceutically acceptable carrier.

20. A pharmaceutical composition comprising a therapeutically effective amount of a compound of claim 12 and a pharmaceutically acceptable carrier.

21. A method of preparing an iodide C;

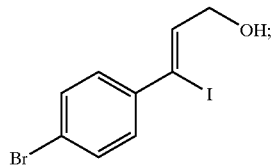
(C)

comprising:

a) reducing intermediate B

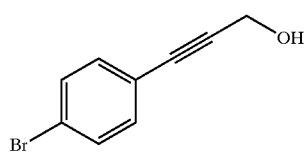
(B)

with sodium bis(2-methoxyethoxy)aluminum hydride (Red-Al); and b) treating the resulting intermediate with iodine to give the iodide C.

22. A method of preparing an intermediate D;

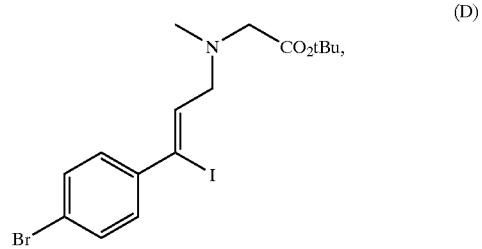
(D)

comprising:

a) reducing intermediate B

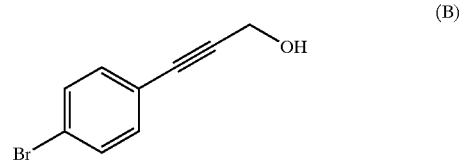
(B)

with sodium bis(2-methoxyethoxy)aluminum hydride (Red-Al) and treating the resulting intermediate with iodine to give iodide C

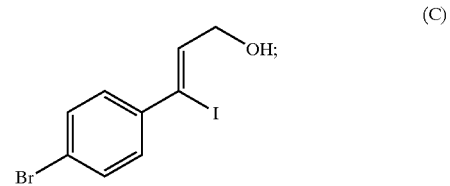
(C)

b) converting the alcohol moiety of iodide C to a bromide; and c) displacing the bromide with sarcosine t-butyl ester to the provide intermediate D.

23. The method of claim 22, wherein the conversion of step (b) comprises treatment with N-bromosuccinimide and triphenylphosphine.

24. A method of preparing an intermediate E

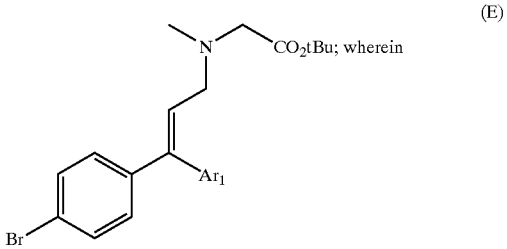
(E)

$Ar_1$ is thienyl optionally substituted by up to one methyl or ethyl, the method comprising:

a) reducing intermediate B

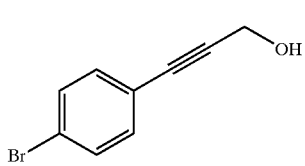

with sodium bis(2-methoxyethoxy)aluminum hydride (Red-Al) and treating the resulting intermediate with iodine to give iodide C

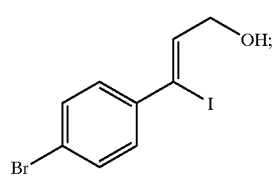

b) converting the alcohol moiety of iodide C to a bromide;

c) displacing the bromide with sarcosine t-butyl ester to provide an intermediate D

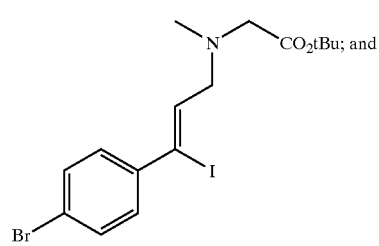

d) coupling the intermediate D with a boronic acid of the formula $Ar_1B(OH)_2$, wherein $Ar_1$ is as described above, in the presence of a palladium (0) catalyst to give the intermediate of the formula E.

25. The method of claim 24, wherein the conversion of step (b) comprises treatment with N-bromosuccinimide and triphenylphosphine.

26. A method of preparing a compound of the formula G

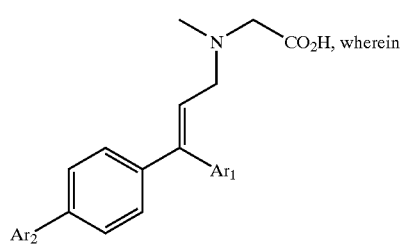

$Ar_1$ is thienyl optionally substituted by up to one methyl or ethyl, and $Ar_2$ is selected from the group consisting of thienyl, furyl and substituted phenyl, wherein phenyl substituents are selected from $C_{1-6}$ alkyl, halo, $C_{1-6}$ haloalkyl, $C_{1-6}$ alkoxy, $C_{1-6}$ haloalkoxy, and cyano;

the method comprising:

a) reducing intermediate B

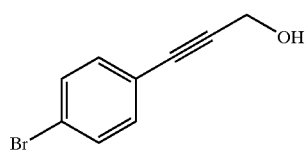

with sodium bis(2-methoxyethoxy)aluminum hydride (Red-Al) and treating the resulting intermediate with iodine to give iodide C

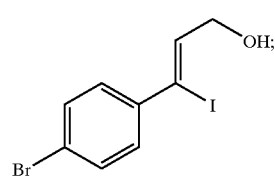

b) converting the alcohol moiety of iodide C to a bromide;

c) displacing the bromide with sarcosine t-butyl ester to provide intermediate D

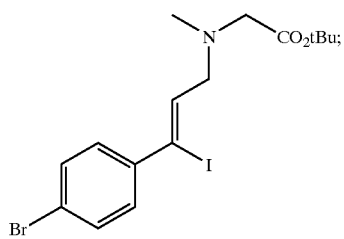

d) coupling intermediate D with a boronic acid of the formula $Ar_1B(OH)_2$, wherein $Ar_1$ is as described above, in the presence of a palladium (0) catalyst to give an intermediate of the formula E

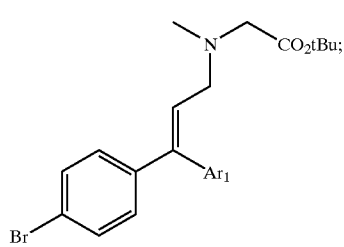

e) coupling intermediate E with an aryl boronic acid of the formula $Ar_2B(OH)_2$, wherein $Ar_2$ is as described above, in the presence of a palladium (0) catalyst to give intermediate F

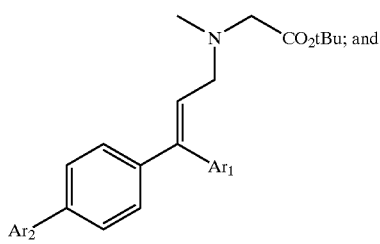

f) hydrolyzing the ester group of the intermediate F to give the compound of the formula G.

27. The method of claim 26, wherein the conversion of step (b) comprises treatment with N-bromosuccinimide and triphenylphosphine.

28. The method of claim 27, wherein the hydrolysis of step (f) comprises treatment with formic acid.

29. A compound of the formula C, D or E

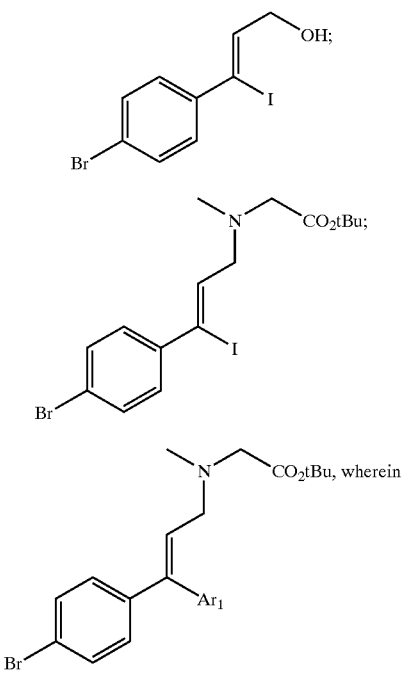

$Ar_1$ is thienyl optionally substituted by up to one methyl or ethyl.

30. A method for treating a patient having a medical condition for which a glycine transport inhibitor is indicated, comprising the step of administering to the patient a pharmaceutical composition as defined in claim 17.

31. A method according to claim 30 in which the medical condition is schizophrenia.

32. A method according to claim 31 wherein wherein $Ar_1$ of the compound is 2-thiophene.

33. A method according to claim 32 wherein the compound according to formula 1 $Ar_1$ is 2-(3-methylthiophene).

34. A method according to claim 31, wherein in the compound according to formula 1 $Ar_1$ is 3-thiophene.

35. A method according to claim 31, wherein in the compound according to formula 1 $Ar_1$ is 3-(4-methylthiophene).

36. A method according to claim 31, wherein in the compound according to formula 1 $Ar_2$ is substituted phenyl where the substituent is selected from $CF_3$, Me, iPr, MeO, CN, and $CF_3O$.

37. A method according to claim 31, wherein in the compound according to formula 1 $Ar_2$ is furan.

38. A method according to claim 31, wherein in the compound according to formula 1 $Ar_2$ is thiophene.

39. A method according to claim 31, wherein the compound according to formula 1 is selected from the group consisting of:

(Z)-N-(1-(4-(4-Isopropylphenyl)phenyl)-1(3-thienyl)prop-1 -en-3-yl)sarcosine;

(Z)-N-(1-(4-(3-Thienyl)phenyl)-1-(3-thienyl)prop-1-en-3-yl)sarcosine;

(Z)-N-(1-(4-(2-Thienyl)phenyl)1-(3-thienyl)prop-1-en-3-yl)sarcosine;

(Z)-N-(1-(4-(2-Furyl)phenyl)1-(3-thienyl)prop-1-en-3-yl)sarcosine;

(Z)-N-(1-(4-(3-Methoxyphenyl)phenyl)1-(3-thienyl)prop-1-en-3-yl)sarcosine;

(Z)-N-(1-(4-(3-Methylphenyl)phenyl)-1-(3-thienyl)prop-1-en-3-yl)sarcosine;

(Z)-N-(1-(4-(3-(Trifluoromethoxy)phenyl)phenyl)1-(3-thienyl)prop-1-en-3-yl)sarcosine;

(Z)-N-(1-(4-(3-Cyanophenyl)phenyl)1-(3-thienyl)prop-1-en-3yl)sarcosine;

(Z)-N-(1-(4-(3-Thienyl)phenyl-1(2thienyl)prop-1-en-3-yl)sarcosine;

(Z)-N-(1-(4-(3-Thienyl)phenyl)-1-(3-(4-methylthienyl))prop-1-en-3-yl)sarcosine;

(Z)-N-(1-(4-(3-(Trifluoromethyl)phenyl)phenyl)-1(3-(4-methylthienyl))prop-1-en-3-yl)sarcosine;

(Z)-N-(1-(4-(3-Methoxyphenyl)phenyl)1-(3-(4-methylthienyl))prop-1-en-3-yl)sarcosine; and (Z)-N-(1-(4-(3-Methylphenyl)phenyl)1-(2-(3-methylthienyl))propyl-1-en-3-yl)sarcosine.

40. A method according to claim 31, wherein the compound according to formula 1 is (Z)-N-(1-(4-(3-Thienyl)phenyl)-1-(2-methylphenyl)prop-1-en-3-yl)sarcosine.

41. A method according to claim 31, wherein the compound according to formula 1 is (Z)-N-(1-(4-(2-Furyl)Phenyl)-1-(3-thienyl)prop-1-en-3-yl)sarcosine.

42. A method according to claim 31, wherein the compound according to formula 1 is (Z)-N-(1-(4-(4-Isopropylphenyl)phenyl)-1-(3-thienyl)prop-1-en-3-yl)sarcosine.

43. A method according to claim 30 in which the medical condition is cognitive dysfunction.

44. A method according to claim 43, wherein wherein $Ar_1$ of the compound is 2-thiophene.

45. A method according to claim 43, wherein in the compound according to formula 1 $Ar_1$ is 2-(3-methylthiophene).

46. A method according to claim 43, wherein in the compound according to formula 1 $Ar_1$ is 3-thiophene.

47. A method according to claim 43, wherein in the compound according to formula 1 $Ar_1$ is 3-(4-methylthiophene).

48. A method according to claim 43, wherein in the compound according to formula 1 $Ar_2$ is substituted phenyl where the substituent is selected from $CE_3$, Me, iPr, MeO, CN, and $CF_3O$.

49. A method according to claim 43, wherein in the compound according to formula 1 $Ar_2$ is turan.

50. A method according to claim 43, wherein in the compound according to formula 1 $Ar_2$ is thiophene.

51. A method according to claim 43, wherein the compound according to formula 1 is selected from the group consisting of:
- (Z)-N-(1-(4-(4-Isopropylphenyl)phenyl)-1-(3-thienyl) prop-1-en-3-yl)sarcosine;
- (Z)-N-(1-(4-(3-Thienyl)phenyl)-1-(3-thienyl)prop-1-en-3-yl)sarcosine;
- (Z)-N-(1-(4-(2-Thienyl)phenyl)-1-(3-thienyl)prop-1-en-3-yl)sarcosine;
- (Z)-N-(1-(4-(2-Furyl)phenyl)-1-(3-thienyl)prop-1-en-3-yl)sarcosine;
- (Z)-N-(1-(4-(3-Methoxyphenyl)phenyl)1-(3-thienyl) prop-1-en-3-yl)sarcosine;
- (Z)-N-(1-(4-(3-Methylphenyl)phenyl)-1-(3-thienyl)prop-1-en-3-yl)sarcosine;
- (Z)-N-(1-(4-(3-(Trifluoromethoxy)phenyl)phenyl)-1-(3-thienyl)prop-1-en-3-yl)sarcosine;
- (Z)-N-(1-(4-(3-Cyanophenyl)phenyl)-1-(3-thienyl)prop-1-en-3-yl)sarcosine;
- (Z)-N-(1-(4-(3-Thienyl)phenyl)-1 -(2-thienyl)prop-1-en-3-yl)sarcosine;
- (Z)-N-(1-(4-(3-Thienyl)phenyl)-1-(3-(4-methylthienyl)) prop-1-en-3-yl)sarcosine;
- (Z)-N-(1-(4-(3-(Trifluoromethyl)phenyl)phenyl)-1-(3-(4-methylthienyl))prop-1-en-3-yl)sarcosine;
- (Z)-N-(1-(4-(3-Methoxyphenyl)phenyl)1-(3-(4-methylthienyl))prop-1en-3-yl)sarcosine; and
- (Z)-N-(1-(4-(3-Methylphenyl)phenyl)-1-(2-(3-methylthienyl))prop-1-en-3-yl)sarcosine.

52. A method according to claim 43, wherein the compound according to formula 1 is (Z)-N-(1-(4-(3-Thienyl)phenyl)-1-(2-methylphenyl)prop-1-en-3-yl)sarcosine.

53. A method according to claim 43, wherein the compound according to formula 1 is (Z)-N-(1-(4-(2-Furyl)phenyl)-1-(3-thienyl)prop-1-en-3-yl)sarcosine.

54. A method according to claim 43, wherein the compound according to formula 1 is (Z)-N-(1-(4-(4-Isopropylphenyl)phenyl)- 1(3-thienyl)prop-1-en-3-yl)sarcosine.

55. A method according to claim which the medical condition is Alzheimer's disease.

56. A method according to claim 55, wherein wherein $Ar_1$ of the compound is 2-thiophene.

57. A method according to claim 55, wherein in the compound according to formula 1 $Ar_1$ is 2-(3-methylthiophene).

58. A method according to claim 55, wherein in the compound according to formula 1 $Ar_1$ is 3-thiophene.

59. A method according to claim 55, wherein in the compound according to formula 1 $Ar_1$ is 3-(4-methylthiophene).

60. A method according to claim 55, wherein in the compound according to formula 1 $Ar_2$ is substituted phenyl where the substituent is selected from $CF_3$, Me, iPr, MeO, CN, and $CF_3O$.

61. A method according to claim 55, wherein in the compound according to formula 1 $Ar_2$ is furan.

62. A method according to claim 55, wherein in the compound according to formula 1 $Ar_2$ is thiophene.

63. A method according to claim 55, wherein the compound according to formula 1 is selected from the group consisting of:
- (Z)-N-(1-(4-(4-Isopropylphenyl)phenyl)-1-(3-thienyl) prop-1 -en-3-yl)sarcosine;
- (Z)-N-(1-(4-(3-Thienyl)phenyl)-1-(3-thienyl)prop-1-en-3-yl)sarcosine;
- (Z)-N-(1-(4-(2-Thienyl)phenyl)-1-(3-thienyl)prop-1-en-3-yl)sarcosine;
- (Z)-N-(1-(4-(2-Furyl)phenyl)-1-(3-thienyl)prop-1-en-3-yl)sarcosine;
- (Z)-N-(1-(4-(3-Methoxyphenyl)phenyl)-1-(3-thienyl) prop-1-en-3-yl)sarcosine;
- (Z)-N-(1-(4-(3-Methylphenyl)phenyl)-1-(3-thienyl)prop-1-en-3-yl)sarcosine;
- (Z)-N-(1-(4-(3-(Trifluoromethoxy)phenyl)phenyl)-1-(3-thienyl)prop-1-en-3-yl)sarcosine;
- (Z)-N-(1-(4-(3-Cyanophenyl)phenyl)-1-(3-thienyl)prop-1-en-3-yl)sarcosine;
- (Z)-N-(1-(4-(3-Thienyl)phenyl)-1-(2-thienyl)prop-1-en-3-yl)sarcosine;
- (Z)-N-(1-(4-(3-Thienyl)phenyl)-1-(3-(4-methylthienyl)) prop-1-en-3-yl)sarcosine;
- (Z)-N-(1-(4-(3-(Trifluoromethyl)phenyl)phenyl)-1-(3-(4-methylthienyl))prop-1-en-3-yl)sarcosine;
- (Z)-N-(1-(4-(3-Methoxyphenyl)phenyl)-1-(3-(4-methylthienyl))prop-1-en-3-yl)sarcosine; and
- (Z)-N-(1-(4-(3-Methylphenyl)phenyl)-1-(2-(3-methylthienyl))prop-1-en-3-yl)sarcosine.

64. A method according to claim 55, wherein the compound according to formula 1 is (Z)-N-(1-(4-(3-Thienyl) phenyl)-1-(2-methylphenyl)prop-1-en-3-yl)sarcosine.

65. A method according to claim 55, wherein the compound according to formula 1 is (Z)-N-(1-(4-(2-Furyl) phenyl)-1-(3-thienyl)prop-1-en-3-yl)sarcosine.

66. A method according to claim 55, wherein the compound according to formula 1 is (Z)-N-(1-(4-(4-Isopropylphenyl)phenyl)-1-(3-thienyl)prop-1-en-3-yl) sarcosine.

* * * * *